(12) United States Patent
Gilboa et al.

(10) Patent No.: US 6,711,429 B1
(45) Date of Patent: *Mar. 23, 2004

(54) SYSTEM AND METHOD FOR DETERMINING THE LOCATION OF A CATHETER DURING AN INTRA-BODY MEDICAL PROCEDURE

(75) Inventors: Pinhas Gilboa, Haifa (IL); David Tolkowsky, Tel Aviv (IL); David Hollander, Raanana (IL)

(73) Assignee: Super Dimension Ltd., Herzelia (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/463,176

(22) PCT Filed: Sep. 24, 1999

(86) PCT No.: PCT/IL99/00512

§ 371 (c)(1),
(2), (4) Date: Jan. 21, 2000

(87) PCT Pub. No.: WO00/16684

PCT Pub. Date: Mar. 30, 2000

Related U.S. Application Data

(63) Continuation-in-part of application No. 09/179,827, filed on Oct. 28, 1998.
(60) Provisional application No. 60/142,976, filed on Jul. 12, 1999.

(30) Foreign Application Priority Data

Sep. 24, 1998 (IL) ................................................ 126333

(51) Int. Cl.[7] ................................................ A61B 5/05
(52) U.S. Cl. ........................ 600/407; 600/424; 607/122
(58) Field of Search ................................ 600/424, 427, 600/411, 372–374, 407; 128/899; 607/122, 115; 606/130

(56) References Cited

U.S. PATENT DOCUMENTS

| 5,042,486 | A |   | 8/1991  | Pfeiler et al. |         |
|-----------|---|---|---------|----------------|---------|
| 5,203,337 | A |   | 4/1993  | Feldman        |         |
| 5,409,000 | A |   | 4/1995  | Imran          |         |
| 5,443,489 | A |   | 8/1995  | Ben-Haim       |         |
| 5,662,108 | A |   | 9/1997  | Budd et al.    |         |
| 5,740,808 | A | * | 4/1998  | Panescu et al. | 600/424 |
| 5,891,134 | A |   | 4/1999  | Goble et al.   |         |
| 6,149,592 | A | * | 11/2000 | Yanof et al.   | 600/427 |
| 6,216,027 | B1| * | 4/2001  | Willis et al.  | 600/424 |
| 6,226,543 | B1| * | 5/2001  | Gilboa et al.  | 600/407 |
| 6,246,899 | B1| * | 6/2001  | Chia et al.    | 600/424 |
| 6,314,310 | B1| * | 11/2001 | Ben-Haim et al.| 600/424 |
| 6,473,635 | B1| * | 10/2002 | Rasche         | 600/428 |
| 6,558,333 | B2| * | 5/2003  | Gilboa et al.  | 600/466 |

FOREIGN PATENT DOCUMENTS

| WO | IL97/00011 | 1/1997 |
| WO | IL97/00058 | 2/1997 |
| WO | IL97/00059 | 2/1997 |
| WO | US97/02650 | 2/1997 |
| WO | IL97/00308 | 9/1997 |
| WO | IL98/00034 | 1/1998 |

* cited by examiner

*Primary Examiner*—Shawna J Shaw
(74) *Attorney, Agent, or Firm*—Mark M. Friedman

(57) ABSTRACT

A system and method of displaying at least one point-of-interest of a body during an intra-body medical procedure. The method is effected by (a) establishing a location of the body; (b) establishing a location of an imaging instrument being for imaging at least a portion of the body; (c) defining at least one projection plane being in relation to a projection plane of the imaging instrument; (d) acquiring at least one point-of-interest of the body; and (e) projection said at least one point-of-interest on said at least one projection plane; such that, in course of the procedure, the locations of the body and the imaging instrument are known, thereby the at least one point-of-interest is projectable on the at least one projection plane even in cases whereby a relative location of the body and the imaging instrument are changed.

347 Claims, 4 Drawing Sheets

SYSTEM AND METHOD FOR DETERMINING THE LOCATION OF A CATHETER DURING AN INTRA-BODY MEDICAL PROCEDURE

This is an national phase filing of PCT application No. PCT/IL99/00512 filed Sep. 25, 1999, which claims priority from Israel Patent Application No. 126,333 filed Sep. 24, 1998, is a continuation-in-part of U.S. patent application Ser. No. 09/179,827 filed Oct. 28, 1998, and which further benefits from the filing date of Provisional U.S. Patent Application No. 60/142,976 filed Jul. 12, 1999.

FIELD AND BACKGROUND OF THE INVENTION

The present invention relates to a system and method of recording and displaying in context of an image a location of at least one point-of-interest in a body during an intra-body medical procedure, and, more particularly, to a system and method which enable to simultaneously obtain location data of the body, of a catheter inserted into the body and of an imaging instrument used to image the catheter and the body, to thereby record and display in context of the image the location of the at least one point-of-interest in a body even when the relative location between any of the above locatable items is changed.

In many cases patients undergo procedures in which a catheter is inserted into their body (e.g., into a body cavity, such as, but not limited to, heart, lung, kidney, liver, bladder and brain cavities). It is in many cases desirable to follow the location of the catheter within the body. This is especially the case when the catheter is a probe designed to collect local information from within the body (e.g., record electrical activity) and/or to perform a local treatment within the body (e.g., ablation). In such cases, it is important to precisely locate the catheter within the body, such that the local information collected has value and/or the treatment is applied at the appropriate location. To this end, methods have been developed in which an imaging apparatus is employed to provide an image of the body, whereas a locating implement combined with location implements (e.g., transmitters or receivers of electromagnetic or acoustic waves) to which the locating implement (receiver or transmitter, respectively) is compatible, and which are attached to the body of the patient and to the tip of the catheter, are employed to determine the location in space of the catheter and preferably also the body of the patient. However, the prior art fails to teach the co-establishment of the location of the imaging apparatus or the image coordinates, such that points-of-interest in the body are recordable, displayable and most importantly projectable onto an image of the body of the patient taken from another angle during the same procedure or during another, later procedure.

The following discussion of prior art, as well as most of the embodiments discussed hereinunder, focus on cardiac applications where the applicability of catheter probes in combination of imaging has found many uses.

About 150,000 patients in the U.S. and about a similar number of patients in other parts of the globe who suffer from cardiac arrhythmia are treated in an electro-physiology (EP) laboratory each year. Most of these patients undergo a procedure in which selected portions of their heart tissue are ablated.

Cardiac arrhythmia is the result of improper progression of electrical signals for contraction along the heart tissue. The common cases of cardiac arrhythmia include accessory pathways, ventricular tachycardia, supra ventricular tachycardia, AV node reentry and atrial tachycardia.

In addition, some atrial fibrillation symptoms, as well as arterial flutter symptoms, are also treated by ablation.

Until recently, fibrillation and non-typical flutter were treated by the implantation of a defibrillator (ICD). However, recent studies show that maze procedures, as well as other forms of tissue ablation, may also be effective.

A typical EP laboratory includes the following equipment: A steerable X-ray transillumination device, typically a C-mount transluminance fluoroscope; an electrocardiogram unit for recording electric signals obtained by ECG and by electrodes inserted into the heart via catheters to record inner heart electric signals; a radio-frequency unit to effect ablation via RF electrode also engaged with one of the catheters; a pacemaking unit, also operable via one of the catheter; and a computer and display unit for recording and presenting in real-time the electric signals derived from the heart of the patient.

Each procedure involves a staff including at least one and typically two physicians, at least one technician, and a nurse. One of the physicians inserts, advances and steers the catheters within the body of the patient, while the other operates the computer and the other equipment. The tips and distal portions of one or more (typically two) reference catheters are inserted into acceptable reference locations within the heart, typically the coronary sinus (CS) and/or to the right ventricular apical (RVA). The reference catheters include electrodes which measure reference electric signals from the inner surface of the heart tissue. The RVA catheter typically also serves to measure signals of the His boundle. A steerable mapping/ablation/pacemaking catheter in also inserted into the heart and serves to collect electric signals for mapping the electrical activity within the heart, for pacemaking and, in some cases, for ablation of selected locations in the heart. These data may be used as an electrophysiology real time imaging of the heart.

During the procedure, the heart region is transilluminated via the transillumination device and the catheters described are inserted into the heart from the inferior vena cava or the superior vena cava to the right atrium and, if so required, through the tricuspid valve to the right ventricle. Operation in the left portion of the heart is performed via Fossa ovalis to the left atrium and further through the Mitral Valve to the left ventricle. In most cases the problem causing cardiac arrhythmia is known and the procedure is pre-planned. Accordingly, electric signal mapping of the region of interest is effected to locate the precise point to be ablated. Following ablation, the heart is typically triggered by the pacemaking unit to a series of contractions to see if the ablation solved the problem. In many cases the ablation procedure is repeated a number of times until a desired result is achieved.

According to the present methodology, knowing the three dimensional location of the steerable catheter tip within the heart cavity depends on a large number of data parameters and visual memorization and is therefore highly subjective. It is clear that movements of the catheter along the transillumination lines (Z axis) are not at all detectable since the image is two dimensional. In addition, the heart tissue itself is transparent to X-rays and it is therefore hardly or not at all imageable. The reference catheters serve an important function in this respect. While the position of the mapping/ablation/pacemaking catheter along the X and Y axes is provided by the transillumination image, the position of that catheter along the Z axis is evaluated by the steering physician according to the electrical signals recorded therefrom as compared to those signals recorded by the reference electrodes. Thus, the three dimensional location of the mapping/ablation/pacemaking catheter is subjectively established by experience, memorization and analysis of a large number of data parameters as opposed to objective criteria. These difficulties are more critical when it is required to return accurately to a location already mapped for further treatment. It is further more critical to be aware of changes in catheter location during ablation, at which time the catheter's own electric signals mapping function must be turned off and therefore it provides no locational indications. In solutions preceding the current invention, completely undetectable and undesirable location shifts during ablation are sometimes experienced.

A catheter which can be located in a patient using an ultrasound transmitter allocated to the catheter is disclosed in U.S. Pat. No. 4,697,595 and in the technical note "Ultrasonically marked catheter, a method for positive echographic catheter position identification." Breyer et al., Medical and Biological Engineering and Computing. May, 1985, pp. 268–271. Also, U.S. Pat. No. 5,042,486 discloses a catheter which can be located in a patient using non-ionizing fields and superimposing catheter location on a previously obtained radiological image of a blood vessel.

There is no discussion in either of these references as to the acquisition of a local information, particularly with electrical activation of the heart, with the locatable catheter tip and of possible superimposition of this local information acquired in this manner with other images, particularly with a heartchamber image.

U.S. Pat. No. 5,443,489 teaches an apparatus and method for the treatment of cardiac arrhythmias directed to a method for ablating a portion of an organ or bodily structure of a patient, which comprises obtaining a perspective image of the organ or structure to be mapped; advancing one or more catheters having distal tips to sites adjacent to or within the organ or structure, at least one of the catheters having ablation ability; sensing the location of each catheter's distal tip using a non-ionizing field; at the distal tip of one or more catheters, sensing local information of the organ or structure; processing the sensed information to create one or more data points; superimposing the one or more data points on the perspective image of the organ or structure; and ablating a portion of the organ or structure.

U.S. Pat. No. 5,409,000 teaches endocardial mapping and ablation system for introduction into a chamber of the heart formed by a wall and having a passage leading thereto comprising a catheter probe having a distal extremity adapted to be positioned in the chamber of the heart. The catheter probe is comprised of a plurality of flexible longitudinally extending circumferentially spaced-apart arms adapted to be disposed within the chamber of the heart. Electrodes are carried by the arms and are adapted to be moved into engagement with the wall of the heart. Markers visible ultrasonically are carried by the arms for encoding the arms so that the one arm can be distinguished from another. An ablation catheter is carried by and is slidably mounted in the catheter probe and has a distal extremity movable into the chamber of the heart while the catheter probe is disposed therein. The ablation catheter has control means whereby the distal extremity can be moved independently of movement of the catheter probe while the distal extremity of the catheter probe is in the chamber of the heart. An ablation electrode is carried by the distal extremity of the ablation catheter. Ultrasonic viewing means is carried by the distal extremity of the ablation catheter. The distal extremity of the ablation catheter is movable into positions to view ultrasonically the markers carried by the arms of the catheter probe so that the arms can be identified and the spacing of the arms can be ascertained.

Additional prior art of relevance includes WO 97/25101, WO 98/11840, WO 97/29701, WO 97/29682, WO 97/29685 and U.S. Pat. No. 5,662,108. It will be appreciated that U.S. Pat. Nos. 5,409,000 and 5,662,108, both are incorporated by reference as if fully set forth herein, teach real time electrophysiology imaging.

However, the above cited prior art, and in particular U.S. Pat. No. 5,443,489 and U.S. Pat. No. 5,409,000, which in some aspects of the present invention are considered the closest prior art, fail to teach establishment of the location of the imaging apparatus employed. This, in turn, is associated with a major limitation because it is in many cases advantageous to image the patient from different angles, so as to obtain images of different planes thereof. Yet, any catheter location data (point-of-interest) recorded in context of an image obtained from a certain relative orientation is non-projectable onto images obtained from other orientations, because the location in space of the imaging device is not monitored or established.

In addition, during ablation procedures as described hereinabove, it is in many cases advantageous to know an exact former ablation point, because if the application of ablation was either to an excessively small area, or non-precise, it is required to reablate tissue close to the ablated area. The above apparatuses and methods, while teaching the recording of heart functionality for identifying active sites therein, fail to teach the recording of other points-of-interest, such as, but not limited to, points to which ablation has been applied, therefore preventing the accurate relocation of such sites for nearby ablation as required from time to time.

Furthermore, as further detailed hereinunder, the records, obtained using the above apparatuses and methods, cannot be retrieved and used in later procedures applied to the same patient, whereas according to some of the embodiments according to the present invention such ability is realized.

The ability to record points-of-interest will also find benefits in percutaneous myocardial revascularization (PMR) in which holes are drilled into the heart muscle to provide for the creation of new blood vessels, also known as angiogenesis, in the heart's muscle and particularly in an ischemic portion of the heart's muscle. The exact spacing and positioning of the holes, and potentially their angle relative to the tissue, is crucial and can be monitored using the method and system according to the present invention in a better way as compared with the prior art.

The ability to record points-of-interest will also find benefits in other transcatheter methods for encouraging such angiogenesis, including, but not limited to, cell transplantation and the application of proteins, such as growth hormones to selected regions in the body. The spacing, positioning and/or angle of the application of such treatments are important and can be monitored using the method and system according to the present invention in a better way as compared with the prior art.

The present invention also finds uses and advantages in flexible catheters and flexible electrodes (as opposed to solid instruments or probes) based cerebrovascular and neurosurgical procedures that are performed in combination with some form of imaging. In particular, the present invention is advantageous when corrective procedures are applied to the same patient at a later date, due to the ability to precisely return to an old location where treatment has been applied in the past.

There is thus a widely recognized need for, and it would be highly advantageous to have, a method and system devoid of the above limitations. Especially, there is a widely recognized need for, and it would be highly advantageous to have, a system and method which enable to simultaneously obtain location data of the body of a patient, of a catheter inserted into the body of the patient and of an imaging instrument used to image the catheter and the body, to thereby record and display in context of an image generated by the instrument the location of at least one point-of-interest in the body even when the relative location between any of the above locatable items is changed.

SUMMARY OF THE INVENTION

According to one aspect of the present invention there is provided a method of displaying at least one point-of-interest of a body during an intra-body medical procedure, the method comprising the steps of (a) establishing a location of the body; (b) establishing a location of an imaging instrument being for imaging at least a portion of the body; (c) defining at least one projection plane being in relation to a projection plane of the imaging instrument; (d) acquiring at least one point-of-:interest of the body; and (e) projecting said at least one point-of-interest on said at least one projection plane; such that, in course of the procedure, the locations of the body and the imaging instrument are known, thereby the at least one point-of-interest is projectable on the at least one projection plane even in cases whereby a relative location of the body and the imaging instrument are changed.

According to another aspect of the present invention there is provided a system for recording and displaying at least one point-of-interest of a body during an intra-body medical procedure, the system comprising system of displaying at least one point-of-interest of a body during an intra-body medical procedure, the system comprising (a) a mechanism for establishing a location of the body; (b) a mechanism for establishing a location of an imaging instrument being for imaging at least a portion of the body; (c) a mechanism for defining at least one projection plane being in relation to a projection plane of the imaging instrument; (d) a mechanism for acquiring at least one point-of-interest of the body; and (e) a mechanism for projecting the at least one point-of-interest on the at least one projection plane; such that, in course of the procedure, the locations of the body and the imaging instrument are known, thereby the at least one point-of-interest is projectable on the at least one projection plane even in cases whereby a relative location of the body and the imaging instrument are changed.

According to yet another aspect of the present invention there is provided a method of recording and displaying at least one point-of-interest of a body during an intra-body medical procedure, the method comprising the steps of (a) establishing a location of the body; (b) establishing a location of an imaging instrument being for imaging at least a portion of the body; (c) defining at least one projection plane being in relation to a projection plane of the imaging instrument; (d) inserting a catheter into the portion of the body and establishing a location of the catheter; (e) advancing the catheter to at least one point-of-interest in the portion of the body and recording a location of the at least one point-of-interest; and (f) projecting the at least one point-of-interest on the at least one projection plane; such that, in course of the procedure, the locations of the body and the imaging instrument are known, thereby the at least one point-of-interest is projectable on the at least one projection plane even in cases whereby a relative location of the body and the imaging instrument are changed.

According to still another aspect of the present invention there is provided a system for recording and displaying at least one point-of-interest of a body during an intra-body medical procedure, the system comprising (a) a mechanism for establishing a location of the body; (b) a mechanism for establishing a location of an imaging instrument being for imaging at least a portion of the body; (c) a mechanism for defining at least one projection plane being in relation to a projection plane of the imaging instrument; (d) a mechanism for establishing a location of a catheter insertable into the portion of the body; (e) a mechanism for recording a location of at least one point-of-interest via the location of the catheter by advancing the catheter to the at least one point-of-interest in the portion of the body; and (f) a mechanism for projecting the at least one point-of-interest on the at least one projection plane; such that, in course of the procedure, the locations of the body and the imaging instrument are known, thereby the at least one point-of-interest is projectable on the at least one projection plane even in cases whereby a relative location of the body and the imaging instrument are changed.

According to an additional aspect of the present invention there is provided a method of navigating a catheter's tip to at least one point-of-interest in a body during an intra-body medical procedure, the method comprising the steps of (a) establishing a location of the body; (b) establishing a location of an imaging instrument being for imaging at least a portion of the body; (c) defining at least one projection plane being in relation to a projection plane of the imaging instrument; (d) inserting a catheter into the portion of the body and establishing a location of the catheter; (e) projecting at least a portion of the catheter on the at least one projection plane; (f) acquiring at least one point-of-interest of the portion of the body; (g) projecting the at least one point-of-interest on the at least one projection plane, such that, in course of the procedure, the locations of the body, the catheter and the imaging instrument are known, thereby the at least one point-of-interest and the at least a portion of the catheter are projectable on the at least one projection plane even in cases whereby a relative location of the body and the imaging instrument are changed; and (h) navigating the cathetr's tip to at least one of the points-of-interest.

According to yet an additional aspect of the present invention there is provided a system for navigating a catheter's tip to at least one point-of-interest in a body during an intra-body medical procedure, the system comprising (a) a mechanism for establishing a location of the body; (b) a mechanism for establishing a location of an imaging instrument being for imaging at least a portion of the body; (c) a mechanism for defining at least one projection plane being in relation to a projection plane of the imaging instrument; (d) a mechanism for establishing a location of a catheter being insertable into the portion of the body; (e) a mechanism for projecting at least a portion of the catheter on the at least one projection plane; (f) a mechanism for acquiring at least one point-of-interest of the portion of the body; (g) a mechanism for projecting the at least one point-of-interest on the at least one projection plane, such that, in course of the procedure, the locations of the body, the catheter and the imaging instrument are known, thereby the at least one point-of-interest and the at least a portion of the catheter are projectable on the at least one projection plane even in cases whereby a relative location of the body and the imaging instrument are changed; and (h) a mechanism for navigating the cathetr's tip to at least one of the points-of-interest.

According to further features in preferred embodiments of the invention described below, the system further comprising a mechanism for displaying a virtual image of the at least one point-of-interest in context of at least one image representing the at least one projection plane.

According to still further features in the described preferred embodiments the system further comprising a mechanism for displaying a virtual image of the at least a portion the catheter in context of at least one image representing the at least one projection plane.

According to still further features in the described preferred embodiments displaying the at least a portion of the catheter in context of the at least one image is effected by averaging its location over at least one cardiac cycle and also throughout the cardiac cycle.

According to still further features in the described preferred embodiments displaying the at least a portion of the catheter in context of the at least one image is effected by averaging its location over at least one respiratory cycle.

According to still further features in the described preferred embodiments displaying the at least a portion of the catheter in context of the at least one image is effected by averaging its location throughout a respiratory cycle.

According to still further features in the described preferred embodiments displaying the at least a portion of the catheter in context of the at least one image is effected by averaging its location over at least one respiratory cycle and also throughout the respiratory cycle.

According to still further features in the described preferred embodiments the system further comprising the a mechanism for displaying a virtual image of the at least a portion the catheter in context of the at least one image representing the at least one projection plane.

According to still further features in the described preferred embodiments establishing the location of the body is effected by attaching a location implement onto the body and establishing the location of the body via a locating implement.

According to still further features in the described preferred embodiments the location implement and the locating implement form a locating system selected from the group consisting of electromagnetic locating system, magnetic locating system, acoustic locating system, and stereopair optical system.

According to still further features in the described preferred embodiments establishing the location of the body is effected by ensuring that the body is fixed at a known location during the procedure.

According to still further features in the described preferred embodiments establishing the location of the body is effected by image processing of features in an image provided by the imaging instrument.

According to still further features in the described preferred embodiments the features are imageable markers made in contact with the body.

According to still further features in the described preferred embodiments the markers are distinguishable from one another.

According to still further features in the described preferred embodiments establishing the location of the body is synchronized with a physiological activity of the body.

According to still further features in the described preferred embodiments the catheter includes a plurality of electrodes for simultaneously collecting local electric information from inner walls of a heart cavity.

According to still further features in the described preferred embodiments the catheter includes a strain gauge, a potentiometer and/or any other mechanism for measuring a leverage of a steering mechanism of the catheter.

According to still further features in the described preferred embodiments the catheter includes a location implement locationable via a locating implement.

According to still further features in the described preferred embodiments the location implement and the locating implement form a locating system selected from the group consisting of electromagnetic locating system, magnetic locating system and acoustic locating system.

According to still further features in the described preferred embodiments the imaging instrument is a real-time imaging instrument.

According to still further features in the described preferred embodiments the real-time imaging instrument is selected from the group consisting of ultrasound, fluoroscope, interventional magnetic resonance imaging and electrophysiology imaging.

According to still further features in the described preferred embodiments the imaging instrument is a non-real-time imaging instrument.

According to still further features in the described preferred embodiments the imaging instrument provides a primary image of the portion of the body.

According to still further features in the described preferred embodiments the imaging instrument provides a secondary image of the portion of the body.

According to still further features in the described preferred embodiments the imaging instrument is an electro physiological imaging system.

According to still further features in the described preferred embodiments the imaging instrument is designed to provide an image which corresponds to a vitality map of a tissue.

According to still further features in the described preferred embodiments the imaging instrument is adapted for simultaneously generating at least two images each of a different plane.

According to still further features in the described preferred embodiments the non-real-time imaging instrument is selected from the group consisting of computer aided tomography (CT), magnetic resonance imaging (MRI), positron emission tomography (PET) and three dimensional ultrasound.

According to still further features in the described preferred embodiments establishing the location of the imaging instrument is effected by attaching a location implement onto the imaging instrument and establishing the location of the imaging instrument via a locating implement.

According to still further features in the described preferred embodiments the location implement and the locating implement form a locating system selected from the group consisting of electromagnetic locating system, magnetic locating system, acoustic locating system, and stereopair optical system.

According to still further features in the described preferred embodiments establishing the location of the imaging instrument is effected by image processing of features of the body and by location information regarding the features.

According to still further features in the described preferred embodiments establishing the location of the imaging instrument is effected by image processing of features of the body and by magnification information regarding the features.

According to still further features in the described preferred embodiments the features are imageable markers made in contact with the body.

According to still further features in the described preferred embodiments the features are imageable markers on the at least one catheter.

According to still further features in the described preferred embodiments establishing the location of the imaging instrument is effected by a positioning implement inherent to the imaging instrument.

According to still further features in the described preferred embodiments the portion of the body is a cavity within the body.

According to still further features in the described preferred embodiments the portion of the body is selected from the group consisting of heart, lung, kidney, liver, bladder, brain, colon and a blood vessel.

According to still further features in the described preferred embodiments the virtual image of the at least a portion of the catheter is selected from the group consisting of a virtual image of a at least a portion of the catheter projected on the at least one projection plane, a virtual image of a direction of a portion of the catheter projected on the at least one projection plane, a virtual image of a curvature of at least a portion of the catheter projected on the at least one projection plane and a virtual image of an effect exerted on a tissue by the catheter projected on the at least one projection plane.

According to still further features in the described preferred embodiments the catheter is a probing catheter including at least one sensor.

According to still further features in the described preferred embodiments the at least one sensor is selected from the group consisting of a sensor for sensing bio-physiology signals, a sensor for sensing electro-physiology signals, a sensor for sensing at least one bio-chemical constituent, a sensor for sensing a bio-mechanical effect, a sensor for sensing a physiopathological character of a tissue and an imaging sensor.

According to still further features in the described preferred embodiments the catheter is selected from the group consisting of a steerable catheter, a cardiac catheter, an electrophysiology catheter, an ablating catheter and a catheter exerting energy to a tissue.

According to still further features in the described preferred embodiments the catheter includes an injection device.

According to still further features in the described preferred embodiments the injection device includes an injection mechanism for injecting a substance or an object into the portion of the body, the substance or object is selected from the group consisting of a glue, micro-coils, microspheres, a contrast agent, a growth factor and cells.

According to still further features in the described preferred embodiments the energy is selected from the group consisting of electromagnetic energy, non-coherent light energy, laser energy, microwave energy, mechanical energy, sound energy, ultrasound energy, heating energy and cooling energy.

According to still further features in the described preferred embodiments the catheter includes an item selected from the group consisting of a stent delivery device, an expandable balloon, a lead, a mechanism of lead placement, an electrode, a mechanism for electrode placement and a guiding wire.

According to still further features in the described preferred embodiments the catheter is selected from the group consisting of a guiding catheter, an endoscope, a needle, a surgical tool and a drill for drilling in a tissue of the body.

According to still further features in the described preferred embodiments the catheter is selected from the group consisting of a catheter for treating fistulae, a catheter for treating arteriovenous malformation (AVM), a catheter for treating aneurism, a catheter for treating stenosis, a a catheter for treating sclerosis, a catheter for treating ischemia, a catheter for treating cardiac arrhytmia, a catheter for treating tremor, a catheter for treating Parkinson's disease, a catheter for treating a tumor (either benign or malignant), a catheter for treating renal calculus or a catheter for treating stomach ulcer.

According to still further features in the described preferred embodiments the at least one point-of-interest is a reference point which is useful in context of a medical procedure and a point, a size and shape of which is indicative of treatment range applied.

According to still further features in the described preferred embodiments a plurality of the at least one point-of-interest are arranged in a line.

According to still further features in the described preferred embodiments the line is selected from the group consisting of a closed line, e.g., a circle, a boundary line of an internal organ or a portion thereof, a line taken at a given direction along a body tissue and a boundary line between portions of a tissue having different bio-physiologic characteristic.

According to still further features in the described preferred embodiments the bio-physiologic characteristic is selected from the group consisting of tissue vitality level, tissue blood perfusion level, tissue temperature level, tissue movement characteristic, tissue density level, tissue texture, tissue chemistry, tissue optical transparency level, local pressure level in the body portion and tissue impedance level.

According to still further features in the described preferred embodiments the at least one point-of-interest is selected from the group consisting of a portion of a blood vessel, a junction between at least two blood vessels and a displacement relative to another point-of-interest.

According to still further features in the described preferred embodiments the medical procedure is for treating a medical condition selected from the group consisting of fistulae, arteriovenous malformation (AVM), aneurysm, stenosis, sclerosis, ischemia, cardiac arrhythmia, tremor, Parkinson's disease, malignant tumor and a benign tumor.

According to yet a further aspect of the present invention there is provided a method of determining an angle between a surface of a body cavity and a catheter, the method comprising the steps of (a) establishing a location of the body; (b) defining a plurality of projection planes of the body; (c) inserting the catheter into the body cavity and establishing a location of the catheter; (d) projecting at least a portion of the catheter on each of the plurality of projection planes; and (e) projecting at least one line along the surface on the plurality of projection planes; such that, in course of guiding the catheter, the location of the body, the catheter and the line are known, thereby an angle between the catheter and the line is definable.

According to still a further aspect of the present invention there is provided a system for determining an angle between a surface of a body cavity and a catheter, the system comprising (a) a mechanism for establishing allocation of the body; (b) a mechanism for defining a plurality of projection planes of the body; (c) a mechanism for establishing a location of a catheter insertable into the body cavity; (d) a mechanism for projecting lo at least a portion of the catheter on each of the plurality of projection planes; and (e) a mechanism for projecting at least one line along the surface on the plurality of projection planes; such that, in course of guiding the catheter, the location of the body, the catheter and the line are known, thereby an angle between the catheter and the line is definable.

According to further features in preferred embodiments of the invention described below, the plurality of projection planes include at least two mutually perpendicular planes.

According to still further features in the described preferred embodiments the method further comprising the step of displaying a virtual image of the catheter on at least one of the plurality of projection plane, whereas the system further comprising a mechanism of displaying a virtual image of the catheter on at least one of the plurality of projection plane.

According to still further features in the described preferred embodiments the method further comprising the step of displaying a virtual image of the line on at least one of the plurality of projection plane, whereas the system further comprising a mechanism for displaying a virtual image of the line on at least one of the plurality of projection plane.

According to still further features in the described preferred embodiments the method further comprising the step of displaying a virtual image of the line on at least one of the plurality of projection plane, thereby displaying an angle between the catheter and the line, whereas the system further comprising a mechanism for displaying a virtual image of the line on at least one of the plurality of projection plane, thereby displaying an angle between the catheter and the line.

According to another preferred embodiment of the present invention a mechanism is provided for displaying a virtual image of the at least a portion the catheter in context of at least one image representing the at least one projection plane.

According to still further features in the described preferred embodiments, the virtual image of the at least a portion of the catheter is selected from the group consisting of a virtual image of a at least a portion of the catheter projected on the at least one projection plane, a virtual image of a direction of a portion of the catheter projected on the at least one projection plane, a virtual image of a curvature of at least a portion of the catheter projected on the at least one projection plane and a virtual image of an effect exerted on a tissue by the catheter projected on the at least one projection plane.

According to still further features in the described preferred embodiments the catheter is selected from the group consisting of a steerable catheter, a cardiac catheter, an electrophysiology catheter, an ablating catheter and a catheter exerting energy to a tissue.

According to still further features in the described preferred embodiments the catheter includes an injection device.

According to still further features in the described preferred embodiments the injection device includes an injection mechanism for injecting a substance or an object into the portion of the body, the substance or object is selected from the group consisting of a glue, micro-coils, microspheres, a contrast agent, a growth factor and cells.

According to still further features in the described preferred embodiments the energy is selected from the group consisting of electromagnetic energy, non-coherent light energy, laser energy, microwave energy, mechanical energy, sound energy, ultrasound energy, heating energy and cooling energy.

According to still further features in the described preferred embodiments the catheter includes an item selected from the group consisting of a stent delivery device, an expandable balloon, a lead, a mechanism of lead placement, an electrode, a mechanism for electrode placement and a guiding wire.

According to still further features in the described preferred embodiments the catheter is selected from the group consisting of a guiding catheter, an endoscope, a needle, a surgical tool and a drill for drilling in a tissue of the body.

According to still further features in the described preferred embodiments the at least one point-of-interest is a reference point which is useful in context of a medical procedure and a point, a size and shape of which is indicative of treatment range applied.

According to still further features in the described preferred embodiments a plurality of the at least one point-of-interest are arranged in a line.

According to still further features in the described preferred embodiments the line is selected from the group consisting of a closed line, aboundary line of an internal organ or a portion thereof, a line taken at a given direction along a body tissue and a boundary line between portions of a tissue having different bio-physiologic characteristic.

According to still further features in the described preferred embodiments the bio-physiologic characteristic is selected from the group consisting of tissue vitality level, tissue blood perfusion level, tissue temperature level, tissue movement characteristic, tissue density level, tissue texture, tissue chemistry, tissue optical transparency level, local pressure level in the body portion and tissue impedance level.

According to still further features in the described preferred embodiments the at least one point-of-interest is selected from the group consisting of a portion of a blood vessel, a junction between at least two blood vessels and a displacement relative to another point-of-interest.

According to still an additional aspect of the present invention there is provided a method of recording and displaying in context of an image a location of at least one point-of-interest in a body during an intra-body medical procedure, the method comprising the steps of (a) establishing a location of the body; (b) inserting at least one catheter into a portion of the body, the at least one catheter including a first location implement; (c) using an imaging instrument for imaging the portion of the body; (d) establishing a location of the imaging instrument; (e) advancing the at least one catheter to at least one point-of-interest in the portion of the body and via a locating implement recording a location of the at least one point-of-interest; and (f) displaying and highlighting the at least one point-of-interest in context of an image of the portion of the body, the image being generated by the imaging instrument; such that, in the course of the procedure, the locations of the body, the at least one catheter and the imaging instrument are known, thereby the at least one point-of-interest is projectable and displayable in context of the image even in cases whereby a relative location of the body and the imaging instrument are changed.

According to a further aspect of the present invention there is provided a system for recording and displaying in context of an image a location of at least one point-of-interest in a body during an intra-body medical procedure, the system comprising (a) a first mechanism for establishing a location of the body; (b) at least one catheter insertable into a portion of the body, the at least one catheter being supplemented with a first location implement; (c) an imaging instrument for imaging the portion of the body; (d) a locating implement for locating the first location implement and for establishing a location of the at least one catheter; and (e) a second mechanism for establishing a location of the imaging instrument; such that, by inserting the at least one catheter into the portion of the body; using the imaging instrument for imaging the portion of the body; establishing a location of the imaging instrument; advancing the at least one catheter to at least one point-of-interest in the portion of the body and recording a location of the at least one point-of-interest; so that in the course of the procedure, the locations of the body, the at least one catheter and the imaging instrument are known, the at least one point-of-interest is projectable and displayable in a highlighted fashion in context of an image of the portion of the body generated by the imaging instrument even in cases where a relative location of the body and the imaging instrument are changed.

According to further features in preferred embodiments of the invention described below, the method further comprising the step of displaying a curvature of at least a portion of the catheter on the image.

According to still further features in the described preferred embodiments the at least a portion of the catheter includes a distal portion of the catheter.

According to still further features in the described preferred embodiments the portion of the body is a heart, the method further comprising the step of displaying the at least one catheter in context of the image.

According to still further features in the described preferred embodiments displaying the at least one catheter in context of the image is effected by averaging its location over at least one cardiac cycle.

According to still further features in the described preferred embodiments displaying the at least one catheter in context of the image is effected by monitoring and displaying the catheter's location throughout a duration of a cardiac cycle.

According to still further features in the described preferred embodiments displaying the at least one catheter in context of the image is effected by monitoring and displaying the catheter's location throughout a duration of a cardiac cycle and also averaging its location over at least one cardiac cycle.

According to still further features in the described preferred embodiments displaying the at least one catheter in context of the image is effected by monitoring and displaying the catheter's location throughout a respiratory cycle and also averaging its location over at least one respiratory cycle.

According to still further features in the described preferred embodiments the portion of the body is a heart, the at least one catheter includes two catheters at least one of which is an ablation catheter, the method serves for ablating an origin of cardiac arrhythmia.

According to still further features in the described preferred embodiments a location of cardiac arrhythmia is determined by an intersection of at least two directions formed between the two catheters when probing the heart.

According to still further features in the described preferred embodiments a tissue plane or structure is displayed in context of the image.

According to further features in preferred embodiments of the invention described below, the first mechanism includes a second location implement attachable onto the body, whereas establishing the location of the body is effected via the locating implement.

According to still further features in the described preferred embodiments the second location implement and the locating implement form a locating system selected from the group consisting of electromagnetic locating system, magnetic locating system, acoustic locating system, and stereopair optical system.

According to still further features in the described preferred embodiments the first mechanism is effected by ensuring that the body is fixed at a known location during the procedure.

According to still further features in the described preferred embodiments the first mechanism is effected by image processing of features in the image.

According to still further features in the described preferred embodiments the features are imageable markers made in contact with the body.

According to still further features in the described preferred embodiments the first mechanism is synchronized with a physiological activity of the body.

According to still further features in the described preferred embodiments the at least one catheter includes a probing catheter.

According to still further features in the described preferred embodiments the at least one catheter having an ablation ability.

According to still further features in the described preferred embodiments the at least one catheter includes a sensor for sensing local information within the body.

According to still further features in the described preferred embodiments the at least one catheter includes a plurality of electrodes simultaneously collecting local electric information from inner walls of a heart cavity. In one example, the catheter includes a plurality of flexible longitudinally expanding circumferentially spaced-apart arms adapted to be disposed within a chamber of a heart. In another it includes an inflatable balloon supplemented with such electrodes.

According to still further features in the described preferred embodiments the at least one catheter includes a strain gauge, a potentiometer and/or any other mechanism for measuring a leverage of a steering mechanism of the catheter.

According to still further features in the described preferred embodiments the at least one catheter includes a plurality of first location implements along at least a part of its length, each of the plurality of first location implements is locationable via the locating implement.

According to still further features in the described preferred embodiments the first location implement and the locating implement form a locating system selected from the group consisting of electromagnetic locating system, magnetic locating system and acoustic locating system.

According to still further features in the described preferred embodiments the imaging instrument is a real-time imaging instrument.

According to still further features in the described preferred embodiments the real-time imaging instrument is selected from the group consisting of ultrasound, fluoroscope interventional magnetic resonance imaging and electrophysiology imaging.

According to still further features in the described preferred embodiments the imaging instrument is a non-real-time imaging instrument.

According to still further features in the described preferred embodiments the imaging instrument provides a primary image of the portion of the body.

According to still further features in the described preferred embodiments the imaging instrument provides a secondary image of the portion of the body.

According to still further features in the described preferred embodiments the imaging instrument is an electro physiological imaging system.

According to still further features in the described preferred embodiments the imaging instrument is designed to provide an image which corresponds to a vitality map of a tissue.

According to still further features in the described preferred embodiments the imaging instrument is adapted for simultaneously generating at least two images each of a different plane.

According to still further features in the described preferred embodiments the non-real-time imaging instrument is selected from the group consisting of computer aided tomography (CT), magnetic resonance imaging (MRI), positron emission tomography (PET) and three dimensional ultrasound.

According to still further features in the described preferred embodiments the second mechanism is effected by attaching a second location implement onto the imaging instrument and establishing the location of the imaging instrument via the locating implement.

According to still further features in the described preferred embodiments the second location implement and the locating implement form a locating system selected from the group consisting of electromagnetic locating system, magnetic locating system, acoustic locating system, and stereopair optical system.

According to still further features in the described preferred embodiments the second mechanism is effected by image processing of features in the image and by location information regarding the features.

According to still further features in the described preferred embodiments the features are imageable markers made in contact with the body.

According to still further features in the described preferred embodiments the features are imageable markers on the at least one catheter.

According to still further features in the described preferred embodiments the second mechanism is effected by a positioning implement inherent to the imaging instrument.

According to still further features in the described preferred embodiments the at least one point-of-interest is within a heart in the body.

According to still further features in the described preferred embodiments the at least one catheter has treatment ability, whereas the at least one point-of-interest is at least one point treated by the at least one catheter.

According to still further features in the described preferred embodiments the treatment is ablation or percutaneous myocardial revascularization (PMR), cell transplantation or the application of a growth hormone.

According to still further features in the described preferred embodiments the at least one point-of-interest is at least one point located at a displacement relative to the at least one point treated by the at least one catheter.

According to still further features in the described preferred embodiments the at least one catheter includes a sensor for sensing local information within the body, whereas the at least one point-of-interest is established in accordance with the local information.

According to still further features in the described preferred embodiments the portion of the body is a cavity within the body.

According to still further features in the described preferred embodiments the portion of the body is selected from the group consisting of heart, lung, kidney, liver, bladder, brain, colon and blood vessels.

According to still further features in the described preferred embodiments at least one of the locations is determined in at least three degrees of freedom.

According to still further features in the described preferred embodiments at least one of the locations is determined in at least four degrees of freedom.

According to still further features in the described preferred embodiments at least one of the locations is determined in at least five degrees of freedom.

According to still further features in the described preferred embodiments at least one of the locations is determined in at least six degrees of freedom.

According to still further features in the described preferred embodiments the at least one point-of-interest is highlighted in a distinctive fashion indicative of its nature or properties.

According to still further features in the described preferred embodiments the at least one point-of-interest includes a plurality of points-of-interest all having a common nature or property and are highlighted by a line connecting there amongst.

It will be appreciated that the information of the points-of-interest or of a landmark highlighted thereby is three-dimensional by nature. Thus, using the appropriate algorithms one can generate two images designed for three dimensional perception of depth by a viewer. Such images can, for example, be effected via the use of filtered or polarized light in combination with appropriate filtering or polarizing eye glasses worn by the viewer. Alternatively, head mounted display can be used to provide each eye of the viewer with a required image. In both cases, the viewer acquires a depth perception of the points of interest or landmarks highlighted thereby.

According to still further features in the described preferred embodiments the system further comprising (f) at least one additional imaging instrument for imaging the portion of the body; and (g) a third mechanism for establishing a location of the at least one additional imaging instrument, so as to enable displaying and highlighting the at least one point-of-interest in context of at least one additional image of the portion of the body, the at least one additional image being generated by the at least one additional imaging instrument; such that, in the course of the procedure, the locations of the body, the at least one catheter are known, thereby the at least one point-of-interest is projectable and displayable in context of the at least one additional image even in cases whereby a relative location of the body is changed.

According to still further features in the described preferred embodiments the image and the at least one additional image are projected in predetermined relativity.

According to still further features in the described preferred embodiments displaying and highlighting the at least one point-of-interest is effected in a context of at least two images of the portion of the body, the at least two images being generated by the imaging instrument or by a plurality, e.g., a pair, of imaging instruments, each is of a different plane of the portion of the body.

According to still further features in the described preferred embodiments the at least two images are displayed simultaneously.

According to still further features in the described preferred embodiments the at least two images are of at least two orthogonal planes.

According to still further features in the described preferred embodiments the system further comprising a memory module for receiving and storing in memory the image data and/or the at least one point-of-interest data.

According to still further features in the described preferred embodiments the locating implement is connected to the imaging instrument.

According to another aspect of the present invention there is provided an ablation device comprising (a) a first RF coil for generating ablating RF; (b) a second RF coil for sensing the ablating RF; (c) a comparator for comparing a sensed RF and a predetermined threshold.

According to yet another aspect of the present invention there is provided an ablation system comprising (a) an ablation catheter having an ablation tip; (b) a locating system being operative with the catheter, so as to provide a location of at least the ablation tip is space; (c) a mechanism for monitoring a location of the ablation tip in space when ablation being applied thereby, and for either reporting an operator or automatically terminating an applied ablation when a location of the ablation tip spatially deviates beyond a predetermined threshold from its location.

According to still another aspect of the present invention there is provided a method of evaluating a shape or size of an effectively ablated region during an ablation procedure, the method comprising the steps of (a) contacting an ablation catheter to a tissue to be ablated; (b) ablating the tissue by operating the ablation catheter, while at the same time, monitoring a location of the ablation catheter in respect to an ablated tissue and an actual power being emitted from or absorbed by the ablation catheter as a function of time, thereby, taking into account at least an ablation power dissipation function of the tissue, and optionally also the angle of the catheter's tip relative to the tissue, determining the shape and/or size of the effectively ablated region during the ablation procedure.

The present invention successfully addresses the shortcomings of the presently known configurations by providing a system and method which enable the co-locating of a body of a patient, of a catheter inserted into a portion therein and of an imaging instrument imaging that portion, such that points-of-interest are projectable among images of different planes or sources.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
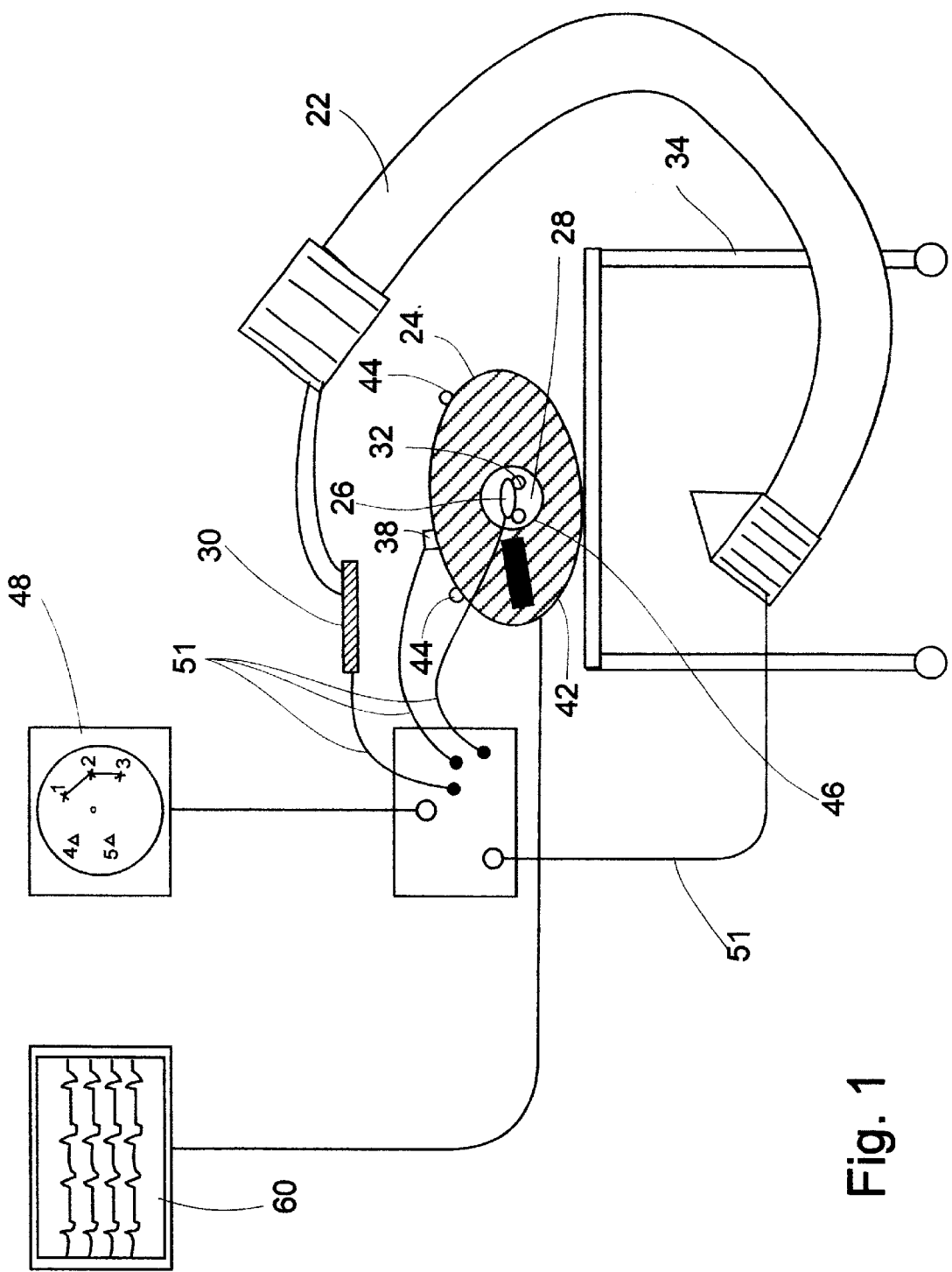
FIG. 1 is a schematic cross-sectional depiction of a preferred embodiment of a system according to the present invention.

The present invention is of a system and method which enable to simultaneously obtain location data of the body, of a catheter inserted into the body and of an imaging instrument used to image the catheter and the body which can be used to simultaneously obtain location data of the body, of the catheter inserted into the body and of the imaging instrument used to image the catheter and the body. Specifically, the present invention can be used to record and display in context of an image the location of the at least one point-of-interest in a body even when the relative location between any of the above locatable items has changed.

The principles and operation of a system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. For example, as used herein the term "catheter" refers both to flexible and to rigid tools, probes, electrodes, endoscopes, needles, such as injection needles, and the like, which are inserted into a body of a patient during a medical or surgical procedure.

Figure 2:
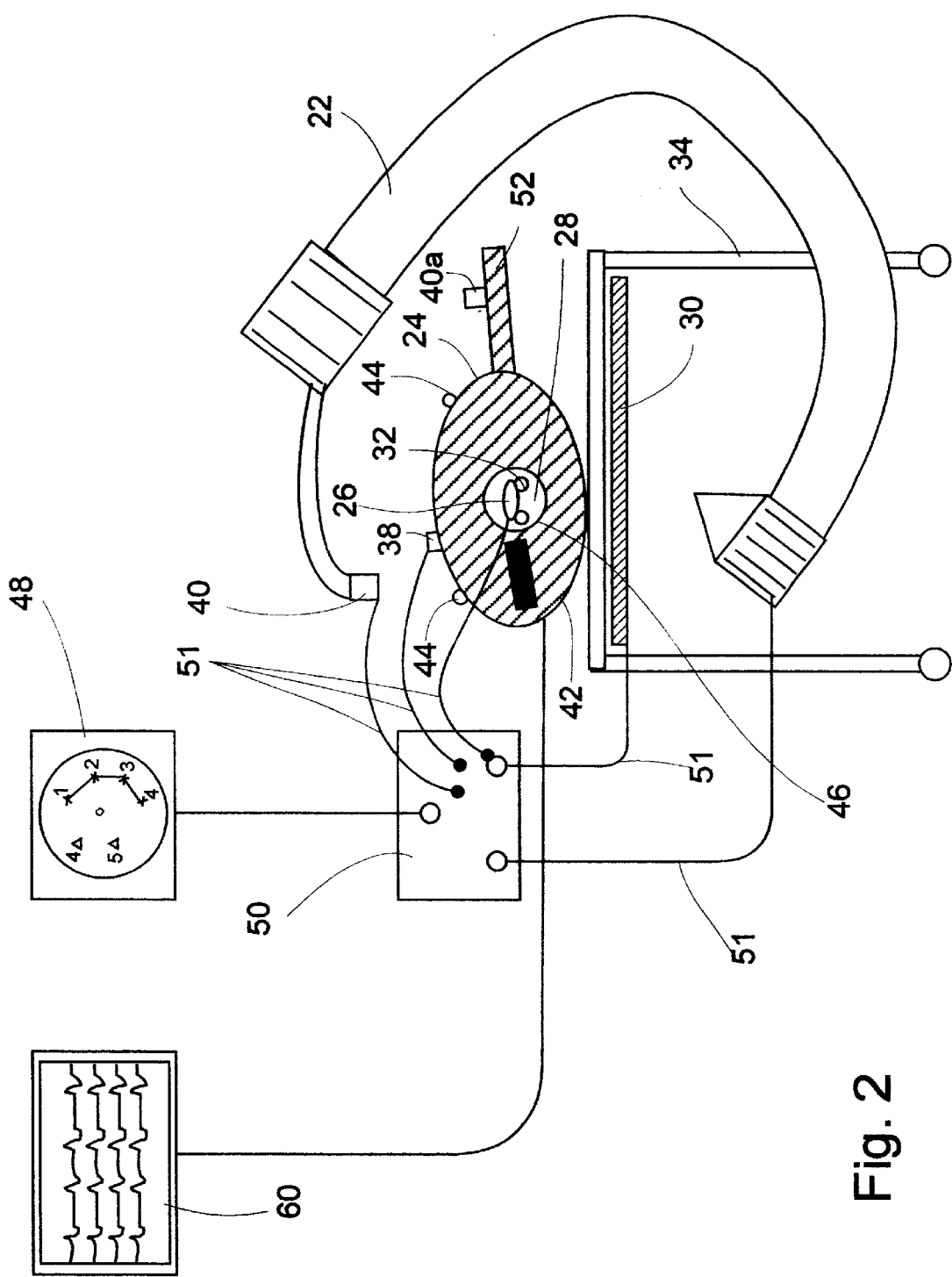
FIG. 2 is a schematic cross-sectional depiction of another preferred embodiment of a system according to the present invention.

Referring now to the drawings, FIGS. 1 and 2 illustrate the present invention in a non-limiting fashion. Thus, according to the present invention there is provided a system for recording and displaying in context of an image a location of at least one point-of-interest in a body during an intra-body medical procedure, which system is referred to herein as system 20. System 20 includes an imaging instrument 22 for imaging a portion of a body of a patient, indicated by 24. System 20 further includes a catheter 26 insertable into in body 24, e.g., into a cavity 28 present in body 24.

As use herein in the specification and in the claims section below, the term "imaging instrument" refers both to a single instrument and to a plurality of instruments of the same or different nature.

As used herein in the specification and in the claims section below, the term "cavity" refers to any hollow in the body, including, for example, cavities of the blood system, such as blood vessels and the heart, cavities of the respiratory system such as the lung cavity and the respiratory ducts, cavities of the digestion system, cavities of the urination system, etc.

As used herein in the specification and in the claims section below, the term "location" refers to a position of a point relative to a reference frame of coordinates, in two or preferably three-dimensions, in at least, for example, two or three degrees of freedom.

The gist of the present invention includes the ability to determine the relative locations among body 24, catheter 26 and imaging instrument 22, such that (i) points-of-interest within body 24 can be presented (highlighted) in context of an image provided by instrument 22; (ii) such points-of-interest are presentable in context of images of different projections, obtained by one or more imaging instruments, or as a side-by-side presentation (still in context), at one, or more time points before or after the logging of a point-of-interest, in other words, such points-of-interest are projectable among all such images or in a separate representation and allow a physician to, for example, go back to a point-of-interest logged in or recorder earlier, in context of an image plane or direction no longer presented; (iii) such points-of-interest are recordable in a memory and can be used in following procedures of the same patient performed, for example, in a different time or place; and (iv) in cases where the cavity itself is non-imageable, such as the heart chambers using a fluoroscope, such points-of-interest can be used to mark some reference cavity coordinates, which will help the user to know the whereabouts within the body cavity and will shorten the procedure and will also reduce the amount of radiation to which the patient and treating staff are exposed to because, the imaging instrument can be shut off for longer time periods during the procedure, or, the imaging instrument can be shut off altogether for the remaining of the procedure, once such points-of-interest are collected and recorded.

This aim is achieved in part according to the present invention by a locating system. The locating system includes a/locating implement 30 (typically a transmitter or receiver of electromagnetic or acoustic waves and location implement or implements 32 (typically receiver(s) or transmitter (s) of electromagnetic or acoustic waves). Implement or implements 32 are engaged at one or plurality of locations along catheter 26, typically close to or at a tip thereof and provide location data in three or more (say four, preferably five, more preferably six) degrees of freedom of catheter 26 with respect to implement 30. Implement 30 can be located in a variety of locations. It can be anywhere within an effective distance with respect to implement(s) 32. As shown in FIG. 1, it can be implemented on imaging instrument 22. In this case, the location of catheter 26 can be determined in relation to instrument 22. As shown in FIG. 2, it can be implemented onto an operation platform 34 on which the patient lies during the medical procedure. U.S. Pat. No. 5,443,489 provides examples for receivers/transmitters which function as herein described.

This aim is further achieved in part according to the present invention by establishing the location of body 24. As shown in FIGS. 1–2, according to an embodiment of the present invention at least one location implement 38 is attached to an external location on body 24, such as on the chest or back side of body 24, or positioned at any desirable position within body 24 of the patient, such that the location of body 24 with respect to implement 30 is establishable in three or more (say four, preferably five, more preferably six) degrees of freedom. Attaching the location implement according to one embodiment is to one or more reference catheters inserted, for example, during cardiac procedures into the heart cavity of the patient and left unmoved therein, all as further detailed in the Background section above. According to the present invention, the location of body 24 can alternatively be determined by image processing of features in the body image obtained via the imaging instrument using, for example, pattern recognition, edge enhancement, edge detection, shape detection and the like techniques of image recognition or processing. These features can be imageable markers 44 (e.g., two or more, two are shown in FIGS. 1–2) attached thereto in known positions. Four or five appropriately distributed, and preferably distinguishable, markers, say small metal discs of differential radius, readily provide location information in six degrees of freedom (X, Y, Z, α, β and γ). Alternatively, the location of body 24 can be fixed at a known location during the procedure and therefore be known. The marks and/or location implements employed can be relocated on the body of the patient in their exact former position by permanently or transiently marking the positions thereof on the body of the patient with, for example, durable ink or tattoo. Image processing or recognition techniques are well known in the art and require no further description herein. In any case, establishing the location of body 24 can be synchronized with a physiological activity of the body which causes the body or portions thereof to rhythmically move, such as breathing and heart beating.

This aim is further achieved in part according to the present invention by establishing the location of imaging instrument 22. In a configuration wherein implement 30 is in physical contact with instrument 22, as for example shown in FIG. 1, its location serves as a reference and it is therefore known. In a configuration wherein implement 30 is not in physical contact with instrument 22, as for example shown in FIG. 2, instrument 22 can include at least one location implement 40, such that the location of instrument 22 with respect to implement 30 is establishable in three or more (say four, preferably five, more preferably six) degrees of freedom. Establishing the location of instrument 22 can also be effected according to the present invention by marking catheter 26 with imageable markers 46 combined with data of its own location and image processing. Establishing the location of the imaging instrument can alternatively be effected by a positioning implement inherent to the imaging instrument. For example, magnetic resonance imaging systems include such inherent positioning implement. Such implements record movements of parts of the instrument relative to a fixed reference coordinate system. As specifically shown in FIG. 2, according to the present invention an additional imaging instrument 52 can be employed along with instrument 22 to obtain additional images of body 24. The location of instrument 52 is established in a fashion similar to that of instrument 22, such that points-of-interest can be projected onto such additional images. A location implement 40 a similar to implement 40 can be employed to establish the location of instrument 52. Alternatively, image processing as described above with respect to instrument 22 can be employed for establishing the location of instrument 52.

According to a preferred embodiment of the present invention locating implement 30 and any of the above location implements 32, 38 and/or 40 form a locating system selected from the group consisting of electromagnetic locating system, magnetic locating system and acoustic locating system. In the case of extra-body location implements, e.g., implements 38 and 40, a stereopair optical system is also applicable. U.S. Pat. Nos. 5,443,489 and 5,662,108; and WO 97/25101, WO 98/11840, WO 10 97/29701, WO 97/29682 and WO 97/29685 and IL patent application No. 125626, filed Aug. 2, 1998, by the present inventor, all of which are incorporated by reference as if fully set forth herein, describe these options, which options are therefore not further described herein in detail. The presently preferred option is the one disclosed in IL patent applications No. 125626 because it enables to determine all of the location information required, as herein described, using a single system.

According to this embodiment of the present invention the relative locations of the body, catheter inserted therein and the imaging instrument are established. As a result, points-of-interest to which the catheter points can be recorded. Such points can thereafter be presented in context of an image taken from any orientation, because the orientation is known. Thus, by inserting the catheter into a portion of the body of the patient, using the imaging instrument for imaging that portion of the body; establishing a location of the imaging instrument; advancing the catheter (e.g., the tip thereof) to a point-of-interest in the portion of the body and recording a location of that point, so that in the course of the procedure, the locations of the body, the catheter and the imaging instrument are known, as well as the magnification employed by the imaging instrument, the point-of-interest is projectable and displayable in a highlighted fashion in context of an image of the portion of the body generated by the imaging instrument even and especially in cases where a relative location of the body and the imaging instrument are changed.

According to another aspect of the present invention there is provided a method of recording and displaying in context of an image a location of at least one point-of-interest in a body during an intra-body medical procedure. The method is effected by implementing the following method steps, in which, in a first step, the location of the body is established. In a second step of the method, at least one catheter including a location implement is inserted into a portion of the body. In a third step of the method, an imaging instrument is used for imaging the portion of the body. In a fourth step the location of the imaging instrument is established. In a fifth step, the catheter is advanced to a point-of-interest in the portion of the body and via a locating implement a location of the point-of-interest is recorded. Whereas, in a sixth step, the point-of-interest is displayed and highlighted in context of an image of the portion of the body, the image is generated by the imaging instrument. As a result, in the course of the procedure, the locations of the body, the catheter and the imaging instrument are known, thereby the point-of-interest is projectable and displayable in context of the image of the portion of the body even in cases whereby a relative location of the body and the imaging instrument are changed.

According to another aspect of the present invention there is provided a method of displaying at least one point-of-interest of a body during an intra-body medical procedure. The method is effected by implementing the following method steps, in which, in a first step, a location of the body is established. Second, a location of an imaging instrument which serves for imaging at least a portion of the body is also established. Third, at least one projection plane which is in relation (i.e., 0–360°) to a projection plane of the imaging instrument is defined. Fourth, at least one point-of-interest of the body is acquired and is projected on the at least one projection plane, such that, in course of the procedure, the locations of the body and the imaging instrument are known, thereby the at least one point-of-interest is projectable on the at least one projection plane even in cases whereby a relative location of the body and the imaging instrument are changed.

Accordingly, the present invention also provides a system for recording and displaying at least one point-of-interest of a body during an intra-body medical procedure. The system according to this aspect of the present invention comprising a mechanism for establishing a location of the body; a mechanism for establishing a location of an imaging instrument being for imaging at least a portion of the body; a mechanism for defining at least one projection plane being in relation to a projection plane of the imaging instrument; a mechanism for acquiring at least one point-of-interest of the body; and a mechanism for projecting the at least one point-of-interest on the at least one projection plane; such that, in course of the procedure, the locations of the body and the imaging instrument are known, thereby the at least one point-of-interest is projectable on the at least one projection plane even in cases whereby a relative location of the body and the imaging instrument are changed.

According to still another aspect of the present invention there is provided a method of recording and displaying at least one point-of-interest of a body during an intra-body medical procedure. The method according to this aspect of the present invention is effected by implementing the following method steps, in which, in a first step, a location of the body is established. In a second step, a location of an imaging instrument which serves for imaging at least a portion of the body is also established. Third, at least one projection plane which is in relation to a projection plane of the imaging instrument is defined. Fourth, a catheter is inserted into the portion of the body and a location of the catheter is established. Fifth, the catheter is advanced to at least one point-of-interest in the portion of the body and a location of the at least one point-of-interest is recorded. Sixth, the at least one point-of-interest is projected on the at least one projection plane; such that, in course of the procedure, the locations of the body and the imaging instrument are known, thereby the at least one point-of-interest is projectable on the at least one projection plane even in cases whereby a relative location of the body and the imaging instrument are changed.

Accordingly, the present invention also provides a system for recording and displaying at least one point-of-interest of a body during an intra-body medical procedure. The system according to this aspect of the present invention includes a mechanism for establishing a location of the body; a mechanism for establishing a location of an imaging instrument being for imaging at least a portion of the body; a mechanism for defining at least one projection plane being in relation to a projection plane of the imaging instrument; a mechanism for establishing a location of a catheter insertable into the portion of the body; a mechanism for recording a location of at least one point-of-interest via the location of the catheter by advancing the catheter to the at least one point-of-interest in the portion of the body; and a mechanism for projecting the at least one point-of-interest on the at least one projection plane; such that, in course of the procedure, the locations of the body and the imaging instrument are known, thereby the at least one point-of-interest is projectable on the at least one projection plane even in cases whereby a relative location of the body and the imaging instrument are changed.

According to an additional aspect of the present invention there is provided a method of navigating a catheter's tip to at least one point-of-interest in a body during an intra-body medical procedure. The method according to this aspect of the present invention is effected by implementing the following method steps, in which, in a first step a location of the body is established. Second, a location of an imaging instrument used for imaging at least a portion of the body is established. Third, at least one projection plane which is in relation to a projection plane of the imaging instrument is defined. Fourth a catheter is inserted into the portion of the body and a lo location of the catheter is established. Fifth, at least a portion of the catheter is projected on the at least one projection plane, Sixth at least one point-of-interest of the portion of the body is acquired. Seventh, the at least one point-of-interest is projected on the at least one projection plane, such that, in course of the procedure, the locations of the body, the catheter and the imaging instrument are known, thereby the at least one point-of-interest and the at least a portion of the catheter are projectable on the at least one projection plane even in cases whereby a relative location of the body and the imaging instrument are changed; and (h) navigating the cathetr's tip to at least one of the points-of-interest.

Accordingly, the present invention also provides a system for navigating a catheter's tip to at least one point-of-interest in a body during an intra-body medical procedure. The system according to this aspect of the present invention includes a mechanism for establishing a location of the body; a mechanism for establishing a location of an imaging instrument being for imaging at least a portion of the body; a mechanism for defining at least one projection plane being in relation to a projection plane of the imaging instrument; a mechanism for establishing a location of a catheter being insertable into the portion of the body; a mechanism for projecting at least a portion of the catheter on the at least one projection plane; a mechanism for acquiring at least one point-of-interest of the portion of the body; a mechanism for projecting the at least one point-of-interest on the at least one projection plane, such that, in course of the procedure, the locations of the body, the catheter and the imaging instrument are known, thereby the at least one point-of-interest and the at least a portion of the catheter are projectable on the at least one projection plane even in cases whereby a relative location of the body and the imaging instrument are changed; and a mechanism for navigating the cathetr's tip to at least one of the points-of-interest.

According to a preferred embodiment a mechanism is provided for displaying a virtual image of the at least one point-of-interest in context of at least one image representing the at least one projection plane.

According to another preferred embodiment a mechanism is provided for displaying a virtual image of the at least a portion the catheter in context of at least one image representing the at least one projection plane.

According to still another preferred embodiment the virtual image of the at least a portion of the catheter is selected from the group consisting of a virtual image of a at least a portion of the catheter projected on the at least one projection plane, a virtual image of a direction of a portion of the catheter projected on the at least one projection plane, a virtual image of a curvature of at least a portion of the catheter projected on the at least one projection plane and a virtual image of an effect exerted on a tissue by the catheter projected on the at least one projection plane.

According to an embodiment of the present invention, and as is further described and detailed hereinunder, a plurality of points-of-interest are arranged in a line, such as, but not limited to, a closed line, a boundary line of an internal organ or a portion thereof, a line taken at a given direction along a body tissue and a boundary line between portions of a tissue having different bio-physiologic characteristic such as, but not limited to, tissue vitality level, tissue blood perfusion level, tissue temperature level, tissue movement characteristic, tissue density level, tissue texture, tissue chemistry, tissue optical transparency level, local pressure level in the body portion and tissue impedance level.

A point-of-interest according to the present invention can be derived from a portion of a blood vessel, a junction between at least two blood vessels and a displacement relative to another point-of-interest.

According to yet a further aspect of the present invention there is provided a method of determining an angle between a surface of a body cavity and a catheter. The method according to this aspect of the present invention is effected by implementing the following method steps, in which, in a first step, a location of the body is established. Second a plurality of projection planes of the body are defined. Third, the catheter is inserted into the body cavity and its location established. Fourth, at least a portion of the catheter is projected on each of the plurality of projection planes. Fifth, at least one line along the surface is projected on the plurality of projection planes; such that, in course of guiding the catheter, the location of the body, the catheter and the line are known, thereby an angle between the catheter and the line is definable.

Accordingly, the present invention provides a system for determining an angle between a surface of a body cavity and a catheter. The system according to this aspect of the present invention includes a mechanism for establishing a location of the body; a mechanism for defining a plurality of projection planes of the body; a mechanism for establishing a location of a catheter insertable into the body cavity; a mechanism for projecting at least a portion of the catheter on each of the plurality of projection planes; and a mechanism for projecting at least one line along the surface on the plurality of projection planes; such that, in course of guiding the catheter, the location of the body, the catheter and the line are known, thereby an angle between the catheter and the line is definable. According to one, not limiting, embodiment, the plurality of projection planes include at least two mutually perpendicular planes.

According to a preferred embodiment, the above method is further effected by displaying a virtual image of the catheter on at least one of the plurality of projection plane, whereas the system further includes a mechanism of displaying a virtual image of the catheter on at least one of the plurality of projection plane.

According to another preferred embodiment the method is further effected by displaying a virtual image of the line on at least one of the plurality of projection plane, whereas the system further includes a mechanism for displaying a virtual image of the line on at least one of the plurality of projection plane.

According to still another preferred embodiment, the method is further effected by displaying a virtual image of the line on at least one of the plurality of projection plane, thereby displaying an angle between the catheter and the line, whereas the system further includes a mechanism for displaying a virtual image of the line on at least one of the plurality of projection plane, thereby displaying an angle between the catheter and the line.

It will be appreciated that the mathematics which enables the projection of points-of-interest associated with a first system of coordinates to another, is well known and therefore requires no further description herein.

The catheter according to the present invention can be of any type. For example, it can be what is known in the art as probing catheter. As used herein in the specification and in the claims section below, the term "probing catheter" refers to a catheter equipped with a sensor for sensing biological activities (or geometry e.g., by intravascular or intracardiac ultrasound), such as, for example, electrophysiological activities. The catheter is preferably designed to provide a treatment within the body. One such treatment is ablation (e.g., radio frequency (RF) ablation). Another is the intrabody local application of a drug. Steerable ablation catheters, as well as other preferred features used in context of the present invention, are described in U.S. Pat. No. 5,443,489, which is incorporated by reference as if fully set forth herein. Alternatively or additionally, the catheter includes local sensors for sensing local information within the body. One example include electrode sensors to record electric activity within the body. Such sensors, as well as other preferred features used in context of the present invention, are described in U.S. Pat. Nos. 5,662,108 and 5,409,000, both are incorporated by reference as if fully set forth herein. Thus, in accordance with the description in U.S. Pat. No. 5,409,000, the catheter according to one embodiment of the present invention includes a plurality of flexible longitudinally expanding circumferentially spaced-apart arms adapted to be disposed within a chamber of a heart, to thereby simultaneously record electric activity in a plurality of locations within the heart.

Figure 3:
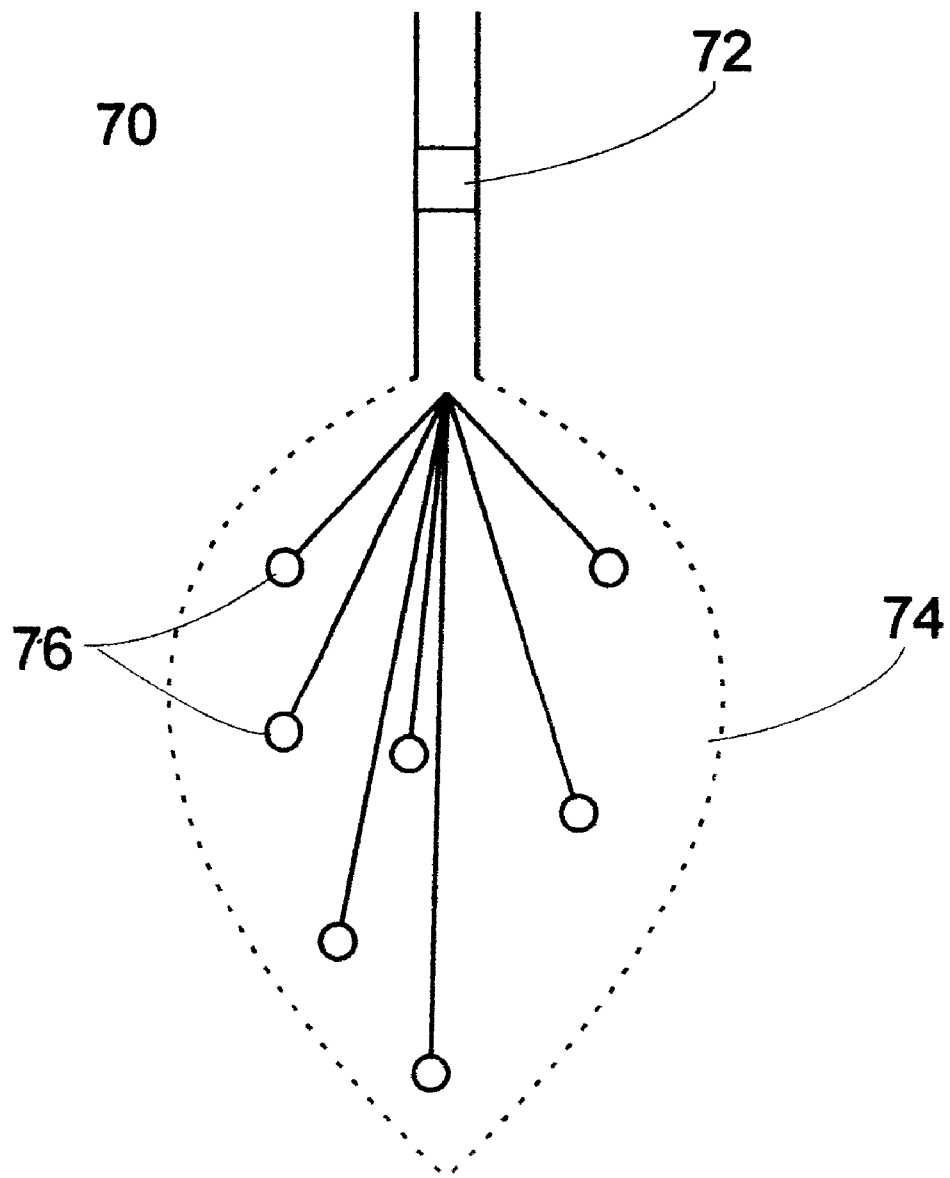
FIG. 3 is a schematic depiction of a catheter including an expandable carrier and a plurality of electrodes according to the present invention.

FIG. 3 shows a catheter 70 including a location implement 72, an expandable carrier 74 implemented at a tip-of catheter 70 and a plurality of electrodes 76 carried by carrier 74.

According to a preferred embodiment of the present invention the catheter is a probing catheter including at least one sensor selected from the group consisting of a sensor for sensing bio-physiology signals, a sensor for sensing electrophysiology signals, a sensor for sensing at least one biochemical constituent, a sensor for sensing a bio-mechanical effect, a sensor for sensing a physiopathological character of a tissue and an imaging sensor.

According to still another preferred embodiment the catheter is selected from the group consisting of a steerable catheter, a cardiac catheter, an electrophysiology catheter, an ablating catheter and a catheter exerting energy to a tissue. According to still another preferred embodiment the catheter includes an injection device which includes an injection mechanism for injecting a substance or an object into the portion of the body, the substance or object is selected from the group consisting of a glue, micro-coils, micro-spheres, a contrast agent, a growth factor and cells.

Any type of energy can be emitted or absorbed by a catheter used to implement the present invention, including, but not limited to, electromagnetic energy, non-coherent light energy, laser energy, microwave energy, mechanical energy, sound energy, ultrasound energy, heating energy and cooling energy.

The catheter used while implementing the present invention may include a stent delivery device, an expandable balloon, a lead, a mechanism of lead placement, an electrode, a mechanism for electrode placement and a guiding wire. The catheter can be a guiding catheter, an endoscope, a needle, a surgical tool and a drill for drilling in a tissue of the body, a catheter for treating a fistulae, a catheter for treating an arteriovenous malformation (AVM), a catheter for treating aneurism, a catheter for treating stenosis, a catheter for treating sclerosis, a catheter for treating ischemia, a catheter for treating cardiac arrhytmia, a catheter for treating tremor, a catheter for treating Parkinson's disease, a catheter for treating a tumor (either benign or malignant), a catheter for treating renal calculus or a catheter for treating stomach ulcer.

According to a preferred embodiment of the invention, in addition to displaying the position and orientation of the catheter's tip, the curvature (bending) of a desired portion of the catheter, and in particular that portion which is adjacent to the catheter tip (i.e., the distal portion) is partially or fully displayed in context of the image. Such information will greatly improve the physician ability to know where the catheter is and steer it in the desired direction. Otherwise, such information is available only under constant use of fluoroscopy, which is undesirable due to the radiation to which both patient and staff are exposed. The location implement placed at the catheter's tip provides its position and orientation. Information about the curvature of the catheter's distal position which precedes the tip can be obtained through, for example, (i) incorporating one or multiple a strain gauges, potentiometers and/or any other mechanisms for measuring a leverage of a steering mechanism of the catheter, into relevant segment(s) of the catheter, the curvature of which is to be monitored; (ii) measuring the leverage of the steering mechanism inherently situated at the proximal end of the catheter; and/or (iii) placing additional location implements throughout the length of the relevant portion(s) of the catheter for which curvature monitoring is desired. Such information on the curvature of the catheter, coupled with information about the position and orientation of the tip thereof, enables the calculation and display of the curvature (bend) of the relevant segment(s) of the catheter, and in particular the catheter's distal segment that precedes the tip on the image. Such display can be effected in a form of, for example, a dashed line or spline, each segment thereof represents an individual segment or portion of the catheter.

According to another preferred embodiment of the present invention continuous synchronization of the catheter tip position to the cardiac pulse is undertaken. According to this embodiment of the present invention, measurement of the location of the catheter's tip when situated against the heart's tissue is taken continuously throughout every cardiac cycle and not only at a specific point in time within such cycle. It will be appreciated in this respect that in currently-known systems that measure a location on the heart's tissue, synchronization of such measurements to the cardiac cycle is performed through gating such location to a known point in time (e.g., the R Wave) in the ECG signal. Such systems include those that reconstruct a three-dimensional image from a collection of imaging planes (e.g., CT, ultrasound), and also those described in, for example, U.S. Pat. No. 5,738,096. Consequently, such measurement requires an accurate synchronization to the cardiac cycle and is updated at a relatively-slow rate of once per cardiac cycle. Conversely, a continuous-averaging method is not dependent on the time of measurement vis-a-vis the cardiac cycle, and also results in a faster update rate of half the duration of a cardiac cycle. Continuous averaging of a collection of measurements taken along the cardiac cycle (systole and dystole collective time period) results in that with every additional measurement of the location of the catheter's tip, that measurement is averaged with all or some of those taken previously during a time period which equals to that of the most-recently-measured cardiac cycle, as measured by ECG signal or from the pulse. It was experimentally found that a display which is most convenient to a physician includes both the current location and orientation of the catheter's tip at any given instant within the cardiac cycle (as the physician is used to seeing the catheter with the fluoroscope), and the average location of that tip when calculated as explained above. Such integrated display greatly facilitates the task of navigating the catheter's tip to any desired location on the heart's tissue. A similar approach can be undertaken to account for body local movements associated with the respiratory cycle, when so required.

The present invention provides means with which locating an origin of a cardiac arrhythmia can be effected more accurately. This feature of the present invention is effected through combination of two measurements taken at different directions on the heart's tissue. It will be appreciated that locating the origin of a cardiac arrhythmia is normally performed with a multi-electrode electrophysiology catheter via a differential measurement two of these electrodes, for example, the ablation electrode placed at the catheter's tip, and an adjacent ring-shaped electrode. Therefore, the arrhythmia's origin is located somewhere along the line connecting the two electrodes. Consequently, selecting the location of the ablation catheter's tip as the desired location for treatment, as is normally done, is not necessarily accurate and may by harmful. According to this embodiment of the present invention, the desired location for treatment (i.e., the origin of cardiac arrhythmia) is marked not only as a point corresponding to the catheter's tip during measurement, but also as a line marking the catheter's direction during that measurement. By performing two measurements taken at two different directions on the heart's tissue, the intersection of the two directions marks the exact origin of the cardiac arrhythmia. This can be effected by the present invention because points-of-interest are provided and memorized thereby, so as to enable to memorize and mark such directions, such that successive measurements can be performed and the positional and electrical information retrieved therefrom used for calculating the exact origin of cardiac arrhythmia.

For cardiac applications the catheter preferably further includes a pacemaking ability (a pacemaking electrode). Catheters effective in cardiac applications according to the present invention are distributed by EP Technologies, San Jose, Calif., U.S.; Cordis Webster Inc., Miami, Fla., U.S.; Cardiac Pathways Corp., Sunnyvale, Calif., U.S.; and Endocardial Solutions Inc., St. Paul, Minn. U.S.

The present invention can be used to provide navigational assistance for directing a tool (e.g., a catheter tip) at an angle to the surface of an intra-body cavity. It will be appreciated that in certain procedures (e.g., endocardial PMR, Gene Therapy or Cell-Based Therapy) the precise directions of an actuator mounted at the end (tip) of a steerable catheter relative to the tissue is essential for success. Providing an intuitive method for manipulating the steerable catheter vis-a-vis the tissue is therefore of great importance. Thus, according to a preferred embodiment of the present invention, in addition to projecting the location and direction of the tip of the catheter on an image plane related to the imaging picture, a line showing the direction in which a local tissue portion is oriented is displayed. The tissue line of direction is an iso-height (i.e., equi-height) curve along the tissue, relative to a reference frame of coordinates. In one preferred embodiment, a display (e.g., numerical and/or virtual-graphical) shows the angle of the catheter's tip (e.g., simulated as a line) relative to two perpendicular planes, each of which is in itself perpendicular to the local tissue plane. In another preferred embodiment the reference frame is in context of the direction of imaging (i.e., the viewing angle of the imaging instrument) in a first view and in a perpendicular direction in a second view; In another preferred embodiment the reference frame is in context of a plane defined by the curvature of the tip of the catheter in a first view, plus an optional perpendicular view. In yet another preferred embodiment the reference frame is in context of the axis of a segment of the catheter.

Several methods are useful for calculating the direction of the tissue. In a first method, the location of at least three points that are not co-planar, placed on the tissue relatively close to each other, should be known. A normal to a plane which contains these points then defines the local direction of the tissue. The location data of these points may be acquired by dragging a catheter equipped with a location implement along a portion of the tissue, or by using an ultrasound probe equipped with a 6 DOF locating system and an appropriate 3D modeling algorithm, as well known in the art and as described herein. In a second method, a line which defines the local direction of the tissue is drawn directly using a catheter equipped with a location implement, by first placing the catheter's tip at a target point, and then drawing a line by dragging the tip while keeping the height constant using a perpendicular view. A third method, which is suitable only in the cavity of the heart, is based on the movement of the tissue during the heart's cardiac cycle. A typical point on the surface of such cavity is moving in an arc path in the course of a cardiac cycle. That arc path is on a virtual plane which is perpendicular to the tissue's surface at that point, and the entire movement is location dependent (i.e., specific to that point). By knowing the characteristic movement and its relation to the direction of the tissue at the site of interest, the latter can be obtained from the former. In this implementation, data is collected by placing the catheter tip at the desired location, measuring the location of the tip during at least one cardiac cycle while synchronizing the data to the cardiac electrophysiology signal, and matching the data to a previously-defined characterization model of movement of the tissue, all for obtaining a normal vector to the local plane of the surface of the inner wall of the heart.

Thus, in intra-cardiac procedures, a physician has to navigate a catheter intra-cardially using fluoroscopic imaging. Orientation of the catheter to a desired location using this type of imaging is difficult since the soft cardiac tissues are not readily imageable, and as such the physician is provided with minimal information as to the structure of the organ. Acquiring information with which a precise boundary line of a cavity within the organ can be generated can significantly increase the physician's ability to correctly orient the catheter during the procedure.

One approach for gathering information required for boundary line generation can be effected by imaging a cavity via either an Intra-Cardiac Ultrasound or a Trans Esophageal Ultrasound. On the basis of the information gathered, a 3D model of the cavity can be constructed. To calculate the boundaries of the cavity in context of a fluoroscope, the 3D model is correlated to the line of sight (viewing angle) of the fluoroscope.

Alternatively, a standard model of the cavity can be used for gathering the information used for calculating the boundaries. Scaling this model to actual size and shape is thus required, and can be performed by matching a few principal points of the model to the corresponding points digitized on the inner surface of the cavity.

In both cases, the model can be presented as a gray level map indicative in each pixel thereof of the depth and/or density of modeled tissue in the line of the respective sight.

While experimenting the present invention it was realized that, in certain occasions, a physician finds it difficult to assimilate the position of the catheter's tip with respect to a 3D imaged of a specific location. In order to assist the physician to assimilate the position of the catheter's tip, according to a preferred embodiment of the present invention, the catheter's tip is projected on a plane traversing the specific location at a predetermined orientation, so as to enable the physician to evaluate the distance between the catheter's tip and the plane. It will be appreciated in this respect that the actual image of the catheter's tip and its projection on a plane as described coincide when the catheter's tip is positioned at the described plane. For example, the plane employed can traverse the tricuspid valve through which the catheter passes when steering the catheter's tip from the right atrium to the right ventricle.

The method and system of the present invention can therefore be utilized to apply gene therapy or cell based therapy, which is performed via injection, by a needle or air pressure, of genetic (e.g., encoding an angiogenesis invoking growth factor) or cell (e.g., induced to invoke angiogenesis) material into the myocardium at a specified angle, to thereby induce myocardial revascularization in an ischemic tissue.

The imaging instrument according to the present invention can be of any type. For example, it can be a real-time imaging instrument, such as, but not limited to, ultrasound, fluoroscope (X-ray transillumination, e.g., a C mount fluoroscope), interventional magnetic resonance imaging (IMRI) and electrophysiology imaging instrument. Alternatively, the imaging instrument is a non-real-time imaging instrument, such as, but not limited to, computer aided tomography (CT), magnetic resonance imaging (MRI), positron emission tomography (PET) and three dimensional ultrasound (a software therefore is obtainable from EchoTech, Munich, Germany).

Thus, according to one embodiment of the present invention, the imaging instrument provides a primary image of a portion of the body of the treated patient.

As used herein in the specification and in the claims section below, the term "primary image" refers to a 2D image of a 3D tissue, where each picture element is achieved by an integral of some characteristic of the tissue along a line.

Whereas, according to another embodiment of the present invention, the imaging instrument provides a secondary image of said portion of the body.

As used herein in the specification and in the claims section below, the term "secondary image" refers to an image map of activity of a tissue, such as spatial physiological activity obtained by electro-physiology (EP) mapping achieved with a physiological imaging system, tissue vitality mapping, etc.

According to a preferred embodiment of the present invention the imaging instrument is adapted for simultaneously generating at least two images each of a different plane. Bi-plane fluoroscopes having two spaced apart X ray sources are well known in the art, and so are multiple plane ultrasound transducers.

As used herein in the specification and in the claims section below, the term "point-of-interest" refers to any point within the body, e.g., a point on an inner side of a heart wall. The point-of-interest can reflect a point featuring local information such as specific type of electric activity. Alternatively or additionally, the point-of-interest can reflect a point to which treatment, e.g., ablation treatment, has been applied. A point-of-interest can also be displaced in known displacement magnitude and orientation from another point-of-interest. Thus, a point-of-interest can be displaced relative to a point previously treated or a point featuring specific local information previously recorded. In any case, according to a preferred embodiment of the present invention the points-of-interest are highlighted and displayed on a display 48. As shown, according to a preferred embodiment of the present invention each of the points-of-interest is highlighted in a distinctive fashion indicative of its nature or properties. Distinctively highlighting points-of-interest according to the present invention can involve application of alphanumeric symbols, shapes, colors, etc. Some or all of the points-of-interest having a common nature or property can be highlighted by a line connecting there amongst. For example, connecting amongst points-of-interest can be employed to highlight anatomical landmarks, such as, but not limited to, a valve or a chamber in the heart. It will be appreciated in this respect that various principles of analytical geometry, such as the definition of a line by two points, or a circle by three, as is typically applied in drawing software used in computer graphics, can be employed in context of the present invention.

A computer 50 receives all the data, for example, via wires 51 (although wireless communication is also applicable), e.g., the image data, the data relating to the locations of the catheter, imaging instrument and the body of the patient, as well as the locations of points-of-interest which are defined by the user by pointing thereon with the catheter and activating a process for their definition as "points-of-interest", and displays the points-of-interest in context of a present or old image on display 48. Computer 50 preferably includes a memory module for receiving and storing in memory the image and/or points-of-interest data for later retrieval. The points-of-interest can be highlighted superimposed on the image in a single display 48, or alternatively, the points-of-interest and the image can be displayed separately in two different displays.

Displaying and highlighting the points-of-interest according to the present invention can be effected in context of two or more images of the portion of the body. These images are generated by one or more imaging instruments and each can represent a different plane (e.g., orthogonal planes) of the portion of the body. Such images can be displayed simultaneously or independently.

Thus, by knowing the image coordinates, the catheter coordinates and the body coordinates, points-of-interest within the body, pointed at by the catheter can be logged in and projected onto the image. Furthermore, old points-of-interest can be projected onto a present or later image, even if taken from a different orientation, therefore presenting a different plane of the body, or taken by a different imaging instrument.

The three dimensional numerical description of any one or more of the points-of-interest according to the present invention is also displayable. The co-localization of the catheter with a displayed point-of-interest can be made recognizable by a special display effect (e.g., blinking) or sound effect. Automatic steering of the catheter is also envisaged.

In cases of cardiac treatment the patient is also monitored via an electrocardiogram (ECG) system 60, as described in more detail in U.S. Pat. No. 5,443,489.

A more intuitive integration of an additional imaging instrument with, for example, a fluoroscope is also provided by the present invention. According to this embodiment of the present invention the image obtained from the additional imaging instrument (e.g., ultrasound) is projected on a plane with desired relativity to that of the fluoroscope (e.g., identical, parallel, orthogonal or otherwise oriented planes). It will be appreciated in this respect that combining the images generated by two different imaging modalities is often useful as the modalities each provide different types of information. Of specific value is combining a fluoroscopy image and an ultrasound image. Fluoroscopy, which is the modality normally used by cardiologists, shows mainly bones and other firm tissues, blood vessels (through use of a contrast agent), and surgical tools. The ultrasound image excels in showing soft tissues (and changes in such tissues), identifying the anatomy of inner cavities (e.g., heart chambers, valves etc.), and analyzing blood flow (via Doppler)—its use in cardiology, for example, via TEE, ICUS or IVUS, can be highly beneficial. Physicians in many disciplines, and cardiologists in particular, are however far less adapt at interpreting the ultrasound image, which is not only very different in its content than that of the fluoroscope but is also planar (as opposed to the fluoroscope which displays a cylindrical volume in two dimensions) and taken with a constantly-moving probe (as opposed to the fluoroscope which is completely stable when anchored at a selected viewing position). Therefore, when the two images, fluoroscopy and ultrasound, are shown without any correction, their integration and assimilation by the physician's mind into valuable data is difficult. Conversely, if the two images can be shown as if taken from the same direction (and optionally at the same zoom level), the task becomes much simpler. Areas and points-of-interest can then be easily identified in the two images—for example, according to their location in the fluoroscopy image, and the physician then knows where, to look for them in the ultrasound image. To effect this embodiment of the present invention a location implement is coupled with the ultrasound probe. Consequently, the position and orientation at which each ultrasound plane was imaged is well known. Such planar image is then projected on a plane relative to that from which the fluoroscopy image is obtained using the appropriate image processing hardware and software. Such planar image, following the appropriate projection and image processing can be overlapped or co-displayed with the fluoroscopy image. An optional calibration procedure, which is required when overlapping the images and is optional otherwise, may also be added by defining the relative zoom at which the two images are displayed. In a preferred embodiment, the is ultrasound image is actually displayed in two orthogonal views, one in the direction of the fluoroscope and the second perpendicular thereto. One ordinarily skilled in the art would know how to operatively assemble a frame grabber and image processing hardware/software in order to reduce to practice this embodiment of the present invention.

It will be appreciated that the present invention enables marking landmarks and other points-of-interest while using a planar image, such as the image of an ultrasound imaging instrument. Identifying three-dimensional areas of interest for assistance in navigation (e.g., anatomical landmark such as a heart valve, inner wall of a chamber of the heart, etc.) or for further treatment (e.g., a tumor or ischemic tissue identified while using a contrast agent, for example). When a 6-DOF locating system is operatively integrated to an imaging device producing a planar image (e.g., an ultrasound probe), then every point-of-interest marked on the image plane becomes a coordinate in a three-dimensional space. A multiplicity of such points can be marked (e.g., with a mouse on the screen on which the planar image is displayed), and then reconstructed into a three-dimensional object. After that, the imaging device with which the original images were generated may no longer be needed for knowing where the target area resides in the three dimensional space, and for navigating various catheters (e.g., probes, tools) into, or relative to, that area.

The present invention can be employed for in advance planning and guidance of treatment along a desired path. This is performed according to preferred embodiments of the present invention by first marking or defining the desired treatment path, which is then followed in the course of actual treatment. It will be appreciated in this context that certain treatments need to be applied along a specific path. Planning such a path and guiding a tool with which the treatment is performed along that path are difficult, particularly in complex three-dimensional areas of tissue within a dynamically-changing organ such a beating heart. A noted example would be a linear or circular ablation in order to treat a cardiac arrhythmia (see below), in which case the application of the treatment also needs to be continuous and with no gaps. Other treatments may not need to be continuous, however may require certain spacing along such path—examples may include PMR (laser therapy), and gene therapy through injection of some genetic substance (e.g., growth factor).

Thus, according to this aspect of the present invention a treatment path is first displayed on the image by connecting points-of-interest defined by the catheter's tip which points are defined along the desired path. In the case of a tool intended for applying a series of focal treatments, such a path may potentially be annotated with notches reflecting the effective range of each discrete, focal point of treatment. The path is then repeated while treatment is applied, potentially with the help of the above-mentioned notches. Should a gap appear to exist, it is then "filled in" through the application of another point of treatment. Following treatment a perimeter range of each point in which treatment has been applied can be displayed along the path.

The present invention enables treating atrial fibrillation by performing a circular or arc-shaped ablation, or multiple focal ablations, around one or more of the openings of the pulmonary veins from within the heart. Most common are the left superior and right superior veins, whereas the left inferior and right inferior are less common. The following steps are involved in executing the procedure according to the present invention.

First, an intracardiac ultrasound probe equipped with a location implement is inserted through the superior vena cava or the inferior vena cava into the right atrial. The probe is employed to image and identify the fossa ovalis of the cardiac septum and the one or more of the openings of the pulmonary veins. The ultrasound image is projected onto the same direction as of the fluoroscope image direction, such that the locations of the fossa ovalis of the cardiac septum and of the one or more of the openings of the pulmonary veins are registered in context of the coordinate system of the fluoroscope. Using a mouse or any other pointing device, the fossa ovalis and the openings of the pulmonary veins are recorded as reference points of interest. The ultrasound probe can now be retracted.

Second, a guiding sheath supplemented with an ejectable needle and equipped with a location implement is inserted through the superior vena cava or the inferior vena cava into the right atrial and the tip thereof is brought to the fossa ovalis by steering the sheath using the information of its location as derived by its location implement and a virtual image of the reference points of the fossa ovalis. Once appropriately positioned, the needle is ejected to puncture the cardiac septum at the fossa ovalis, and the tip of the guiding sheath is inserted into the left atrium.

Third, the needle is retracted and a steerable ablating catheter equipped with a locating sensor is inserted into the left atrium through the guiding sheath, navigated to target using the previously acquired reference points-of-interest and is used to selectively ablate the circumference of one or more of the of the openings of the pulmonary veins.

Prior to ablation, according to preferred embodiments of the present invention, (i) one can use electrical mapping to identify the specific locations to be ablated on or along the opening(s) of the pulmonary veins; and/or (ii) to mark the entire circumference of these opening(s), as further detailed herein, by defining points-or-interest which form closed path(s) around one or more of the openings, and then ablate along that or these circumference(s) until the arrhythmia is stopped.

Radio frequency (RF) ablation is performed by transmitting an electromagnetic wave which is typically 500 kHz in frequency, from a catheter tip to the inner surface of the myocardium. This electromagnetic wave can be auto-sensed by mounting a miniature coil at the tip of the catheter.

Figure 4:
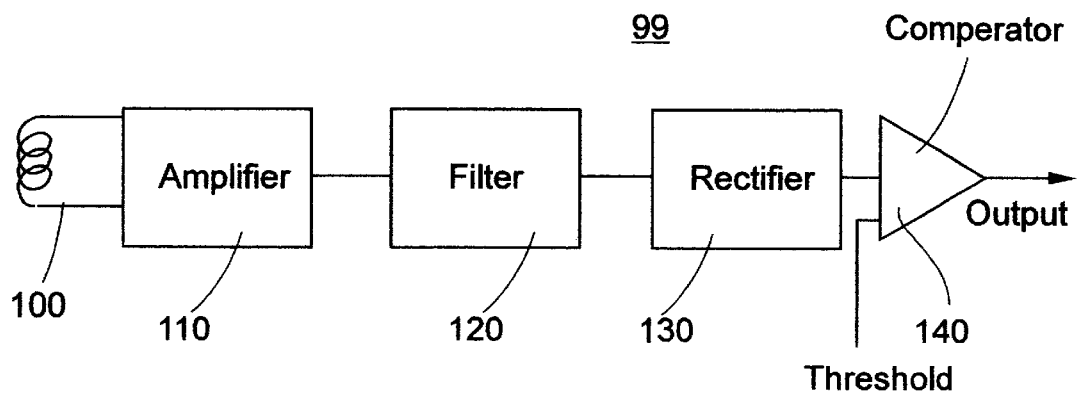
FIG. 4 is a schematic depiction of an auto-sensing apparatus according to the present invention.

FIG. 4 describes the auto-sensing apparatus 99 according to the present invention. An output of a pickup coil 100 is fed to an amplifier 110. The amplified signal is filtered by band-pass filter 120, having a center frequency at the same frequency as the RF current. A rectifier 130 transforms the AC signal to a DC signal. A comparator 140 compares the output level to a predefined threshold. If ablation is effectively applied than the signal is higher than the threshold, and vice versa. Pickup coil 100 can be part of the location implement.

RF-ablation, cryo-ablation and ultrasonic ablation procedures typically prolong at least 30 seconds to complete. During the course of such procedures an ablating catheter tip can and often does displace from the desired treatment location, resulting in an inaccurate, ineffective and often damaging ablation. Thus, by providing the physician with indication of any catheter tip displacement during the course of ablation, the effectiveness of such an ablation procedure can be dramatically increased.

By digitizing the location of a catheter tip at the onset of the procedure, movements of the catheter tip can be tracked. If such movements exceed a predefined threshold, indication is given to the physician which may then halt the procedure. Automatic secession of ablation is also possible. This is of particular importance to myocardial ablation since there are several points on the myocardium such as the AV and SA nodes and the boundle of HIS that are fatal to the patient if accidentally ablated. As such, catheter tip tracking enables close monitoring of the accuracy of the ablation procedure.

Figure 5:
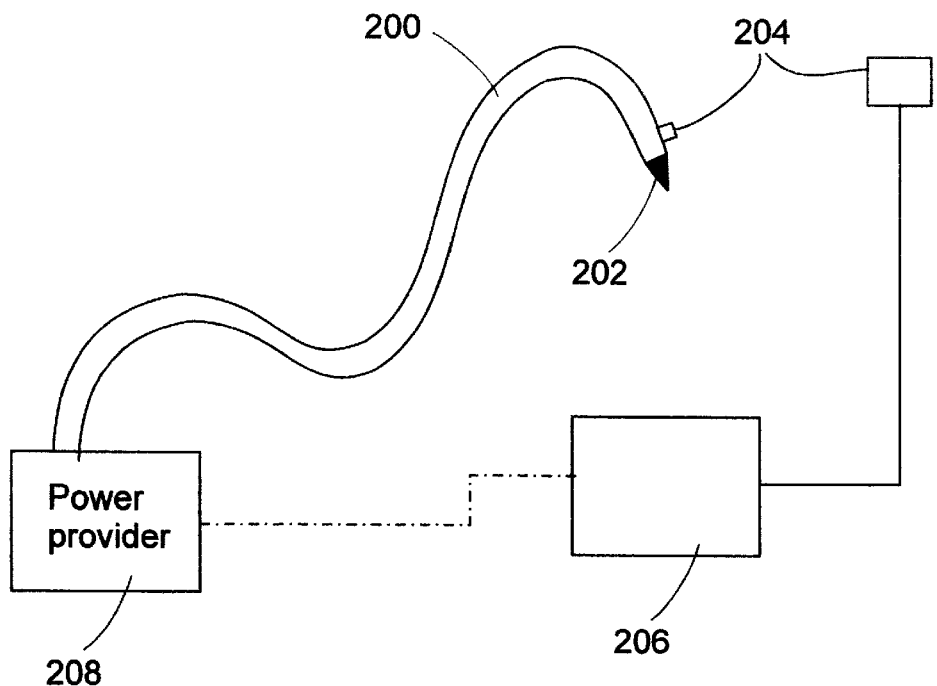
FIG. 5 is a schematic depiction of an ablation system according to the present invention.

An ablation system according to this aspect of the present invention is shown in FIG. 5. The system includes an ablation catheter 200 having an ablation tip 202. In addition, the system further includes a locating system 204 which is operative with catheter 200, so as to provide a location of at least ablation tip 202 is space. The system further includes a mechanism for monitoring a location of ablation tip 202 in space when ablation is applied thereby, and for either reporting an operator or automatically terminating an applied ablation when a location of ablation tip 202 spatially deviates beyond a predetermined threshold from its location. Such a mechanism is realized in FIG. 5 as a computing device 206 which, on one hand, communicated and retrieves information from system 204, and, on the other hand, preferably communicates and commands a power provider 208, e.g., a RF source, of catheter 200. According to a preferred embodiment an auto-sensing apparatus as depicted in FIG. 4 is employed with the system so as to enable determination of ablation start time.

Procedures which utilize radiative energy such as RF, cryo and ultrasonic ablation generate an ablative effect which corresponds to the amount of energy transferred to the tissue, which amount of energy corresponds to the power applied and to the duration of the application. If such energy is provided from a catheter tip which contacts a tissue, then once a point of ablated tissue is achieved, the radius of ablation depends on the energy absorbed by the tissue. When movements of a catheter tip are experienced during the application of ablative treatment to the tissue, a complex shape of ablated region results. By knowing the location of the catheter tip and power transferred to the tissue during ablation, it is possible to estimate the resultant shape and/or size of the tissue effectively ablated.

To do so, the power dissipation from the catheter tip during the course of the procedure, which is dependent upon the cross-section of the power dissipation in the tissue must first be defined. By integrating this power dissipation function, while measuring the transmitted power and location of the tip, an estimation of the resultant shape and/or size of the ablated tissue can be achieved. Some simplification can be applied, since the power dissipated from the catheter tip is assumed to be constant over the time of the procedure. Furthermore, the cross-section of the power dissipation in the tissue can be considered as a constant over a circle of a radius which equals to one point of ablation. Factors such as the angle of the catheter's tip relative to the tissue during ablation may also be taken into account.

In fact, this aspect of the present invention is applicable whenever and wherever energy (e.g., photon energy applied, for example, during photodynamic therapy, etc.) is applied in a regiospecific manner to a tissue of a patient.

Thus, in a broader sense, the present invention provides a method of evaluating an effectively intrabody treated region during a medical procedure. The method according to this aspect of the present invention is executed by (a) contacting a treating catheter to a tissue; and (b) applying treatment to said tissue by operating said catheter, while at the same time, monitoring a location of said catheter in respect to a treated tissue and an actual treatment being applied from said catheter as a function of time, thereby determining the shape or size of the effectively treated region during the medical procedure. Presentation can be, for example, by a virtual image, e.g., along with a virtual image of the catheter itself.

While breathing, the heart is displaced by the diaphragm and lungs in accordance with the respiratory cycle (inhale and exhale). A point-of-interest is preferably acquired while the heart tissue is minimally displaced. Acquiring a point in that exact moment can be done either manually, simply by tracking the movements on the screen, or automatically via a computer.

In the latter case, a signal that is proportional to the respiratory cycle is analyzed and two limit values corresponding to a calculated average and amplitude are defined. A point-of-interest is acquired only when the breathing signal is within the two limit values. For example, an operator may enter, at any point in time, a command to store the location of the tip of a catheter as a point-of-interest, and the point would be stored in memory only when the breathing signal detected is within the two limits. Locating implements attached to the body of the patient can serve as one possible source for breathing signals.

Alternatively, instead of setting limit values to the respiratory cycle induced movements, it is also possible to compensate for such movements.

Initially, the movements of the heart as a function of the respiratory cycle are recorded by monitoring the movements of a catheter's tip contacted to an inner wall in the heart. An assumption is made that the cavity of interest, e.g., the heart, is forced to move uniformly according to pressure exerted from the diaphragm. A location implement of the catheter is contacted with the myocardium and the location thereof is monitored while the component of movement generated from the heart's beating is filtered out by averaging as described above. The resultant movement which depends on respiratory cycle induced movement can be described polynomialy by the movements of the implement.

Once the polynomial coefficients are acquired, the respiratory cycle induced movements at any location inside the cavity can be calculated, and filtered out.

Some ablation catheters include several ablating electrodes positioned along a length thereof. The purpose of such catheters is to generate a series of ablation points which results in a linear ablation pattern. However, if insufficient contact between one or more of the electrode contacts and the tissue occurs, a non-uniform ablation pattern results, and as a result the ablation procedure has to be repeated. In order to minimize damage inflicted to healthy tissue, it is necessary to accurately reposition the catheter in any repeated ablations. In addition, it is sometimes necessary to ablate a linear pattern which is longer than the length generatable by a single application of a multi-electrode catheter. Such a linear pattern can only be obtained by multiple applications which again requires accurate repositioning of the catheter.

By applying two location implements at each end of the length of the catheter along which the ablating electrodes are locate, the curve of this length can be determined, as well as the location of each electrode along this curve. This data can then be used to designate the location of the electrodes as points-of-interest used as reference while ablating.

EXAMPLE

Reference is now made to the following example, which together with the above descriptions, illustrate the invention in a non limiting fashion.

This example is directed at measuring parameters required for fluoroscope imaging according to the present invention.

Assume a first system of coordinates $\{K,L,F\}$ which defines the location of an of an imaging instrument, say a fluoroscope having a source and an imaging plane.

Assume a second system of coordinates $\{X,Y,Z\}$ which defines the location of a location implement.

Define $\{k_0,l_0,f_0\}$ as the origin of the $\{X,Y,Z\}$ system as reflected on the $\{K,L,F\}$ system of coordinates.

The $\{X,Y,Z\}$ system is rotated with respect to the $\{K,L,F\}$ system.

The rotation operator, T, is a matrix of 3×3 terms which satisfies the orthonormality condition.

The location implement implemented in the catheter is at $\{x,y,z\}$ as measured in the $\{X,Y,Z\}$ system.

The location implement is imageable and therefore will be reflected on the image plane of the imaging instrument. The location of its reflection thereon is $\{k,l,f\}$, wherein f is the distance between the radiation source and the image plane, which defines the magnification achieved while imaging.

$$\begin{bmatrix} k \\ l \\ f \end{bmatrix} = \begin{bmatrix} T_{11} & T_{12} & T_{13} \\ T_{21} & T_{22} & T_{23} \\ T_{31} & T_{32} & T_{33} \end{bmatrix} \begin{bmatrix} x \\ y \\ z \end{bmatrix} + \begin{bmatrix} k_0 \\ l_0 \\ f_0 \end{bmatrix} \tag{1}$$

If $\{(k_0,l_0,f_0\}, \{x,y,z\}$, T and f are known, than k and l are:

$$k = f\frac{T_{11}x + T_{12}y + T_{13}z + k_0}{T_{31}x + T_{32}y + T_{33}z + f_0} \tag{2}$$

$$l = f\frac{T_{21}x + T_{22}y + T_{23}z + l_0}{T_{31}x + T_{32}y + T_{33}z + f_0} \tag{3}$$

Thus, the reflection of the tip of the catheter is calculable.

The location of the imaging instrument can be established, as further described hereinabove, via, for example, a location implement. f is, for example, measurable using an additional sensor implemented at the imaging plane.

By simple rearrangement of equations 2 and 3 above, one can obtain a set of homogenous equations:

$$f(T_{11}x+T_{12}y+T_{13}z+k_0)-k(T_{31}x+T_{32}y+T_{33}z+f_0)=0 \tag{4}$$

$$f(T_{21}x+T_{22}y+T_{23}z+l_0)-l(T_{31}x+T_{32}y+T_{33}z+f_0)=0 \tag{5}$$

In addition, because T is an orthonormal matrix, then:

$$T_{11}^2+T_{12}^2+T_{13}^2=1 \tag{6}$$

$$T_{21}^2+T_{22}^2+T_{23}^2=1 \tag{7}$$

$$T_{31}^2+T_{32}^2+T_{33}^2=1 \tag{8}$$

$$T_{11}T_{21}+T_{12}T_{22}+T_{13}T_{23}=0 \tag{9}$$

$$T_{11}T_{31}+T_{12}T_{32}+T_{13}T_{33}=0 \tag{10}$$

$$T_{21}T_{31}+T_{22}T_{32}+T_{23}T_{33}=0 \tag{11}$$

The following Table summarizes the required known parameters (middle column) for calculating unknown parameters (right column) using equations 4–11, wherein the number of measurements (n) required is indicated on the left column:

TABLE

| n | known parameters | required parameter |
|---|---|---|
| 1 | k, l, x, y, z, T, $k_0$, $l_0$ and $f_0$ | f |
| 3 | k, l, x, y, z, $k_0$, $l_0$ and $f_0$ | T |
| 4 | k, l, x, y, z and f | T, $k_0$, $l_0$ and $f_0$ |
| 5 | k, l, x, y and z | T, $k_0$, $l_0$, $f_0$ and f |

It will be appreciated by one ordinarily skilled in the art that the above mathematical description applies to any imaging instrument, including, but not limited to, ultrasound, provided that f, the magnification value thereof is either known or calculable.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of recording and displaying in context of an image a location of at least one point-of-interest in a body during an intra-body medical procedure, the method comprising the steps of:

(a) establishing a location of the body in such a manner as to establish the location of the body even when the body moves;

(b) inserting at least one catheter into a portion of the body, said at least one catheter including a first location implement;

(c) using an imaging instrument for imaging said portion of the body;

(d) establishing a location of said imaging instrument;

(e) advancing said at least one catheter to at least one point-of-interest in said portion of the body and via a locating implement recording a location of said at least one point-of-interest; and (f) displaying and highlighting said at least one point-of-interest in context of an image of said portion of the body, said image being generated by said imaging instrument;

such that, in course of said procedure, said locations of said body, said at least one catheter and said imaging instrument are known, thereby said at least one point-of-interest is projectable and displayable in context of said image even in cases whereby a relative location of said body and said imaging instrument are changed.

2. The method of claim 1, further comprising the step of displaying a curvature of at least a portion of said catheter on said image.

3. The method of claim 2, wherein said at least a portion of said catheter includes a distal portion of said catheter.

4. The method of claim 1, wherein said portion of the body is a heart, the method further comprising the step of displaying said at least one catheter in context of said image.

5. The method of claim 4, wherein displaying said at least one catheter in context of said image is effected by averaging its location over at least one cardiac cycle.

6. The method of claim 4, wherein displaying said at least one catheter in context of said image is effected by monitoring and displaying said catheter's location throughout a duration of a cardiac cycle.

7. The method of claim 4, wherein displaying said at least one catheter in context of said image is effected by monitoring and displaying said catheter's location throughout a duration of a cardiac cycle and also averaging its location over at least one cardiac cycle.

8. The method of claim 4, wherein displaying said at least one catheter in context of said image is effected by monitoring and displaying said catheter's location throughout a respiratory cycle and also averaging its location over at least one respiratory cycle.

9. The method of claim 1, wherein said portion of the body is a heart, said at least one catheter includes two catheters at least one of which is an ablation catheter, the method serves for ablating an origin of cardiac arrhythmia.

10. The method of claim 9, wherein a location of cardiac arrhythmia is determined by an intersection of at least two directions formed between said two catheters when probing said heart.

11. The method of claim 1, wherein a tissue plane or structure is displayed in context of said image.

12. The method of claim 1, wherein establishing said location of the body is effected by attaching a second location implement onto said body and establishing the location of the body via said locating implement.

13. The method of claim 12, wherein said second location implement and said locating implement form a locating system selected from the group consisting of electromagnetic locating system, magnetic locating system, acoustic locating system, and stereopair optical system.

14. The method of claim 1, wherein establishing said location of the body is effected by image processing of features in said image.

15. The method of claim 14, wherein said features are imageable markers made in contact with the body.

16. The method of claim 15, wherein said markers are distinguishable from one another.

17. The method of claim 1, wherein establishing said location of the body is synchronized with a physiological activity of the body.

18. The method of claim 1, wherein said at least one catheter includes a probing catheter.

19. The method of claim 1, wherein said at least one catheter has an ablation ability.

20. The method of claim 1, wherein said at least one catheter includes a sensor for sensing local information within the body.

21. The method of claim 1, wherein said at least one catheter includes a plurality of electrodes for simultaneously collecting local electric information from inner walls of a heart cavity.

22. The method of claim 1, wherein said at least one catheter includes a mechanism for measuring a leverage of a steering mechanism of the catheter.

23. The method of claim 1, wherein said at least one catheter includes a plurality of first location implements along at least a part of its length, each of said plurality of first location implements is locationable via said locating implement.

24. The method of claim 1, wherein said first location implement and said locating implement form a locating system selected from the group consisting of electromagnetic locating system, magnetic locating system and acoustic locating system.

25. The method of claim 1, wherein said imaging instrument is a real-time imaging instrument.

26. The method of claim 25, wherein said real-time imaging instrument is selected from the group consisting of ultrasound, fluoroscope and interventional magnetic resonance imaging.

27. The method of claim 1, wherein said imaging instrument is a non-real-time imaging instrument.

28. The method of claim 27, wherein said non-real-time imaging instrument is selected from the group consisting of computer aided tomography (CT), magnetic resonance imaging (MRI), positron emission tomography (PET) and three dimensional ultrasound.

29. The method of claim 1, wherein said imaging instrument provides a primary image of said portion of the body.

30. The method of claim 1, wherein said imaging instrument provides a secondary image of said portion of the body.

31. The method of claim 1, wherein said imaging instrument is designed to provide an image which corresponds to a vitality map of a tissue.

32. The method of claim 1, wherein said imaging instrument is adapted for simultaneously generating at least two images each of a different plane.

33. The method of claim 1, wherein establishing said location of said imaging instrument is effected by attaching a second location implement onto said imaging instrument and establishing the location of said imaging instrument via said locating implement.

34. The method of claim 33, wherein said second location implement and said locating implement form a locating system selected from the group consisting of electromagnetic locating system, magnetic locating system, acoustic locating system, and stereopair optical system.

35. The method of claim 1, wherein establishing said location of said imaging instrument is effected by image processing of features in said image and by location information regarding said features.

36. The method of claim 35, wherein said features are imageable markers made in contact with the body.

37. The method of claim, 35, wherein said features are imageable markers on said at least one catheter.

38. The method of claim 1, wherein establishing said location of said imaging instrument is effected by image processing of features in said image and by magnification information regarding said features.

39. The method of claim 1, wherein establishing said location of said imaging instrument is effected by a positioning implement inherent to said imaging instrument.

40. The method of claim 1, wherein said at least one point-of-interest is within a heart in said body.

41. The method of claim 1, wherein said at least one catheter has treatment ability, whereas said at least one point-of-interest is at least one point treated by said at least one catheter.

42. The method of claim 41, wherein said treatment is ablation.

43. The method of claim 41, wherein said at least one point-of-interest is at least one point located at a displacement relative to said at least one point treated by said at least one catheter.

44. The method of claim 1, wherein said at least one catheter includes a sensor for sensing local information within the body, whereas said at least one point-of-interest is established in accordance with said local information.

45. The method of claim 1, wherein said portion of the body is a cavity within the body.

46. The method of claim 1, wherein said portion of the body is selected from the group consisting of heart, lung, kidney, liver, bladder, brain, colon and blood vessels.

47. The method of claim 1, wherein at least one of said locations is determined in at least three degrees of freedom.

48. The method of claim 1, wherein at least one of said locations is determined in at least four degrees of freedom.

49. The method of claim 1, wherein at least on of said locations is determined in at least five degrees of freedom.

50. The method of claim 1, wherein at least one of said locations is determined in at least six degrees of freedom.

51. The method of claim 1, wherein said at least one point-of-interest is highlighted in a distinctive fashion indicative of its nature or properties.

52. The method of claim 1, wherein said at least one point-of-interest includes a plurality of points-of-interest all having a common nature or property and are highlighted by a line connecting there amongst.

53. The method of claim 1, further comprising the steps of:
(f) using at least one additional imaging instrument for imaging said portion of the body;
(g) establishing a location of said at least one additional imaging instrument;
(h) displaying and highlighting said at least one point-of-interest in context of at least one additional image of said portion of the body, said at least one additional image being generated by said at least one additional imaging instrument;
such that, in course of said procedure, said locations of said body, said at least one catheter are known, thereby said at least one point-of-interest is projectable and displayable in context of said at least one additional image even in cases whereby a relative location of said body is changed.

54. The method of claim 53, wherein said image and said at least one additional image are projected in predetermined relativity.

55. The method of claim 1, wherein displaying and highlighting said at least one point-of-interest is effected in context of at least two images of said portion of the body, said at least two images being generated by said imaging instrument, each is of a different plane of the portion of the body.

56. The method of claim 55, wherein said at least two images are displayed simultaneously.

57. The method of claim 55, wherein said at least two images are of at least two orthogonal planes.

58. The method of claim 1, further comprising the step of receiving and storing in memory said image data.

59. The method of claim 1, further comprising the step of receiving and storing in memory said image data and said at least one point-of-interest data.

60. The method of claim 1, further comprising the step of receiving and storing in memory said at least one point-of-interest data.

61. The method of claim 1, wherein said locating implement is connected to said imaging instrument.

62. A system for recording and displaying in context of an image a location of at least one point-of-interest in a body during an intra-body medical procedure, the system comprising:
(a) a first mechanism for establishing a location of said body in such a manner as to establish the location of the body even when the body moves;
(b) at least one catheter insertable into a portion of the body, said at least one catheter being supplemented with a first location implement;
(c) an imaging instrument for imaging said portion of the body;
(d) a locating implement for locating said first location implement and for establishing a location of said at least one catheter; and
(e) a second mechanism for establishing a location of said imaging instrument by image processing of features in said image together with magnification information regarding said features;
such that, by inserting said at least one catheter into said portion of the body; using said imaging instrument for imaging said portion of the body; establishing a location of said imaging instrument; advancing said at least one catheter to at least one point-of-interest in said portion of the body and recording a location of said at least one point-of-interest; so that in course of said procedure, said locations of said body, said at least one catheter and said imaging instrument are known, said at least one point-of-interest is projectable and displayable in a highlighted fashion in context of an image of said portion of the body generated by said imaging instrument even in cases where a relative location of said body and said imaging instrument are changed.

63. The system of claim 62, further comprising a third mechanism for displaying a curvature of at least a portion of said catheter on said image.

64. The system of claim 63, wherein said at least a portion of said catheter includes a distal portion of said catheter.

65. The system of claim 63, wherein said third mechanism is selected from the group consisting of multiple strain gauges positioned in segments of said catheter, a steering mechanism of said catheter and multiple additional location implements positioned in segments of said catheter.

66. The system of claim 62, wherein said portion of the body is a heart, the system further comprising a third mechanism for displaying said at least one catheter in context of said image.

67. The system of claim 62, further comprising a third mechanism for displaying said at least one catheter in context of said image by averaging a location of said at least one catheter over at least one cycle of a cyclic movement.

68. The system of claim 62, further comprising a third mechanism for displaying said at least one catheter in context of said image by monitoring and displaying said catheter's location throughout a duration of a cyclic movement.

69. The system of claim 62, further comprising a third mechanism for displaying said at least one catheter in context of said image by monitoring and displaying said catheter's location throughout a duration of a cyclic movement and also averaging its location over at least one cycle.

70. The system of claim 62, wherein said first mechanism includes a second location implement attachable onto said body, whereas establishing said location of the body is effected via said locating implement.

71. The system of claim 70, wherein said second location implement and said locating implement form a locating system selected from the group consisting of electromagnetic locating system, magnetic locating system, acoustic locating system, and stereopair optical system.

72. The system of claim 62, wherein said first mechanism is configured to establish said location of said body by image processing of features in said image.

73. The system of claim 72, wherein said features are imageable markers made in contact with the body.

74. The method of claim 73, wherein said markers are distinguishable from one another.

75. The system of claim 62, wherein said first mechanism is synchronized with a physiological activity of the body.

76. The system of claim 62, wherein said at least one catheter includes a probing catheter.

77. The system of claim 62, wherein said at least one catheter has an ablation ability.

78. The system of claim 62, wherein said at least one catheter includes a sensor for sensing local information within the body.

79. The system of claim 62, wherein said at least one catheter includes a plurality of electrodes for simultaneously collecting local electric information from inner walls of a heart cavity.

80. The system of claim 62, wherein said at least one catheter includes a mechanism for measuring a leverage of a steering mechanism of the catheter.

81. The system of claim 62, wherein said at least one catheter includes a plurality of first location implements along at least a part of its length, each of said plurality of first location implements is locationable via said locating implement.

82. The system of claim 62, wherein said first location implement and said locating implement form a locating system selected from the group consisting of electromagnetic locating system, magnetic locating system and acoustic locating system.

83. The system of claim 62, wherein said imaging instrument is a real-time imaging instrument.

84. The system of claim 83, wherein said real-time imaging instrument is selected from the group consisting of ultrasound, fluoroscope and interventional magnetic resonance imaging.

85. The system of claim 62, wherein said imaging instrument is a non-real-time imaging instrument.

86. The system of claim 62, wherein said imaging instrument provides a primary image of said portion of the body.

87. The system of claim 62, wherein said imaging instrument provides a secondary image of said portion of the body.

88. The system of claim 62, wherein said imaging instrument is designed to provide an image which corresponds to a vitality map of a tissue.

89. The system of claim 62, wherein said imaging instrument is adapted for simultaneously generating at least two images each of a different plane.

90. The system of claim 89, wherein said imaging instrument is selected from the group consisting of computer aided tomography (CT), magnetic resonance imaging (MRI), positron emission tomography (PET) and three dimensional ultrasound.

91. The system of claim 62, wherein said second mechanism is effected by attaching a second location implement onto said imaging instrument and establishing the location of said imaging instrument via said locating implement.

92. The system of claim 91, wherein said second location implement and said locating implement form a locating system selected from the group consisting of electromagnetic locating system, magnetic locating system, acoustic locating system, and stereopair optical system.

93. The system of claim 62, wherein said at least one point-of-interest is within a heart in said body.

94. The system of claim 62, wherein said at least one catheter has treatment ability, whereas said at least one point-of-interest is at least one point treated by said at least one catheter.

95. The system of claim 94, wherein said treatment is ablation.

96. The system of claim 94, wherein said at least one point-of-interest is at least one point located at a displacement relative to said at least one point treated by said at least one catheter.

97. The system of claim 62, wherein said at least one catheter includes a sensor for sensing local information within the body, whereas said at least one point-of-interest is established in accordance with said local information.

98. The system of claim 62, wherein said portion of the body is a cavity within the body.

99. The system of claim 62, wherein said portion of the body is selected from the group consisting of heart, lung, kidney, bladder, liver, brain, colon and blood vessels.

100. The system of claim 62, wherein at least one of said locations is determined in at least three degrees of freedom.

101. The system of claim 62, wherein at least one of said locations is determined in at least four degrees of freedom.

102. The system of claim 62, wherein at least one of said locations is determined in at least five degrees of freedom.

103. The system of claim 62, wherein at least one of said locations is determined in at least six degrees of freedom.

104. The system of claim 62, wherein said at least one point-of-interest is highlighted in a distinctive fashion indicative of its nature or properties.

105. The system of claim 62, wherein said at least one point-of-interest includes a plurality of points-of-interest all having a common nature or property and are highlighted by a line connecting there amongst.

106. The system of claim 62, further comprising:
(f) at least one additional imaging instrument for imaging said portion of the body; and
(g) a third mechanism for establishing a location of said at least one additional imaging instrument, so as to enable displaying and highlighting said at least one point-of-interest in context of at least one additional image of said portion of the body, said at least one additional image being generated by said at least one additional imaging instrument;

such that, in course of said procedure, said locations of said body, said at least one catheter are known, thereby said at least one point-of-interest is projectable and displayable in context of said at least one additional image even in cases whereby a relative location of said body is changed.

107. The system of claim 62, wherein displaying and highlighting said at least one point-of-interest is effected in a context of at least two images of said portion of the body, said at least two images being generated by said imaging instrument, each is of a different plane of the portion of the body.

108. The system of claim 107, wherein said at least two images are displayed simultaneously.

109. The system of claim 107, wherein said at least two images are of at least two orthogonal planes.

110. The system of claim 62, further comprising a memory module for receiving and storing in memory said image data.

111. The system of claim 62, further comprising a memory module for receiving and storing in memory said image data and said at least one point-of-interest data.

112. The system of claim 62, further comprising a memory module for receiving and storing in memory said at least one point-of-interest data.

113. The system of claim 62, wherein said locating implement is connected to said imaging instrument.

114. A method of displaying at least one point-of-interest of a body during an intra-body medical procedure, the method comprising the steps of:
 (a) establishing a location of the body in such a manner as to establish the location of the body even when the body moves;
 (b) establishing a location of an imaging instrument being for imaging at least a portion of the body;
 (c) defining at least one projection plane being in relation to a projection plane of said imaging instrument;
 (d) acquiring at least one point-of-interest of said body; and
 (e) projecting said at least one point-of-interest on said at least one projection plane;
such that, in course of said procedure, said locations of said body and said imaging instrument are known, thereby said at least one point-of-interest is projectable on said at least one projection plane even in cases whereby a relative location of said body and said imaging instrument are changed.

115. The method of claim 114, further comprising the step of displaying a virtual image of said at least one point-of-interest in context of at least one image representing said at least one projection plane.

116. The method of claim 114, wherein said imaging instrument is a three dimensional imaging instrument producing an image by which every picture element represents a coordinate in a three dimensional space, the method further comprising the steps of:
 (f) selecting at least one picture element; and
 (g) calculating a location in said three dimensional space of said picture element.

117. The method of claim 114, wherein establishing said location of the body is effected by attaching a location implement onto said body and establishing the location of the body via a locating implement.

118. The method of claim 117, wherein said location implement and said locating implement form a locating system selected from the group consisting of electromagnetic locating system, magnetic locating system, acoustic locating system, and stereopair optical system.

119. The method of claim 114, wherein establishing said location of the body is effected by image processing of features in an image provided by said imaging instrument.

120. The method of claim 119, wherein said features are imageable markers made in contact with the body.

121. The method of claim 120, wherein said markers are distinguishable from one another.

122. The method of claim 114, wherein establishing said location of the body is synchronized with a physiological activity of the body.

123. The method of claim 114, wherein said imaging instrument is a real-time imaging instrument.

124. The method of claim 123, wherein said real-time imaging instrument is selected from the group consisting of ultrasound, fluoroscope and interventional magnetic resonance imaging.

125. The method of claim 114, wherein said imaging instrument is a non-real-time imaging instrument.

126. The method of claim 125, wherein said non-real-time imaging instrument is selected from the group consisting of computer aided tomography (CT), magnetic resonance imaging (MRI), positron emission tomography (PET) and three dimensional ultrasound.

127. The method of claim 114, wherein said imaging instrument provides a primary image of said portion of the body.

128. The method of claim 114, wherein said imaging instrument provides a secondary image of said portion of the body.

129. The method of claim 114, wherein said imaging instrument is designed to provide an image which corresponds to a vitality map of a tissue.

130. The method of claim 114, wherein said imaging instrument is adapted for simultaneously generating at least two images each of a different plane.

131. The method of claim 114, wherein establishing said location of said imaging instrument is effected by attaching a location implement onto said imaging instrument and establishing the location of said imaging instrument via a locating implement.

132. The method of claim 131, wherein said location implement and said locating implement form a locating system selected from the group consisting of electromagnetic locating system, magnetic locating system, acoustic locating system, and stereopair optical system.

133. The method of claim 114, wherein establishing said location of said imaging instrument is effected by image processing of features of the body and by location information regarding said features.

134. The method of claim 133, wherein said features are imageable markers made in contact with the body.

135. The method of claim 133, wherein said features are imageable markers on said at least one catheter.

136. The method of claim 114, wherein establishing said location of said imaging instrument is effected by image processing of features of the body and by magnification information regarding said features.

137. The method of claim 114, wherein establishing said location of said imaging instrument is effected by a positioning implement inherent to said imaging instrument.

138. The method of claim 114, wherein said portion of the body is a cavity within the body.

139. The method of claim 114, wherein said portion of the body is selected from the group consisting of heart, lung, kidney, liver, bladder, brain, colon and a blood vessel.

140. The method of claim 114, wherein said at least one point-of-interest is selected from the group consisting of a reference point which is useful in context of a medical procedure and a point, a size and shape of which is indicative of treatment range applied.

141. The method of claim 114, wherein a plurality of said at least one point-of-interest are arranged in a line.

142. The method of claim 141, wherein said line is selected from the group consisting of a closed line, a boundary line of an internal organ or a portion thereof, a line taken at a given direction along a body tissue and a boundary line between portions of a tissue having different biophysiologic characteristic.

143. The method of claim 142, wherein said biophysiologic characteristic is selected from the group consisting of tissue vitality level, tissue blood perfusion level, tissue temperature level, tissue movement characteristic, tissue density level, tissue texture, tissue chemistry, tissue optical transparency level, local pressure level in said body portion and tissue impedance level.

144. The method of claim 114, wherein said at least one point-of-interest is selected from the group consisting of a portion of a blood vessel, a junction between at least two blood vessels and a displacement relative to another point-of-interest.

145. The method of claim 114, wherein the medical procedure is for treating a medical condition selected from the group consisting of fistulae, arteriovenous malformation (AVM), aneurysm, stenosis, sclerosis, ischemia, cardiac arrhythmia, tremor, Parkinson's disease, malignant tumor and a benign tumor.

146. A method of recording and displaying at least one point-of-interest of a body during an intra-body medical procedure, the method comprising the steps of:

(a) establishing a location of the body in such a manner as to establish the location of the body even when the body moves;

(b) establishing a location of an imaging instrument being for imaging at least a portion of the body;

(c) defining at least one projection plane being in relation to a projection plane of said imaging instrument;

(d) inserting a catheter into said portion of the body and establishing a location of said catheter;

(e) advancing said catheter to at least one point-of-interest in said portion of the body and recording a location of said at least one point-of-interest; and (f) projecting said at least one point-of-interest on said at least one projection plane;

such that, in course of said procedure, said locations of said body and said imaging instrument are known, thereby said at least one point-of-interest is projectable on said at least one projection plane even in cases whereby a relative location of said body and said imaging instrument are changed.

147. The method of claim 146, further comprising the step of displaying a virtual image of said at least one point-of-interest in context of at least one image representing said at least one projection plane.

148. The method of claim 146, wherein said imaging instrument is a three dimensional imaging instrument producing an image by which every picture element represents a coordinate in a three dimensional space, the method further comprising the steps of:

(g) selecting at least one picture element; and (h) calculating a location in said three dimensional space of said picture element.

149. The method of claim 146, wherein establishing said location of the body is effected by attaching a location implement onto said body and establishing the location of the body via a locating implement.

150. The method of claim 149, wherein said location implement and said locating implement form a locating system selected from the group consisting of electromagnetic locating system, magnetic locating system, acoustic locating system, and stereopair optical system.

151. The method of claim 146, wherein establishing said location of the body is effected by image processing of features in an image provided by said imaging instrument.

152. The method of claim 151, wherein said features are imageable markers made in contact with the body.

153. The method of claim 152, wherein said markers are distinguishable from one another.

154. The method of claim 146, wherein establishing said location of the body is synchronized with a physiological activity of the body.

155. The method of claim 146, wherein said catheter includes a plurality of electrodes for simultaneously collecting local electric information from inner walls of a heart cavity.

156. The method of claim 146, wherein said catheter includes a mechanism for measuring a leverage of a steering mechanism of the catheter.

157. The method of claim 146, wherein said catheter includes a location implement locationable via a locating implement.

158. The method of claim 151, wherein said location implement and said locating implement form a locating system selected from the group consisting of electromagnetic locating system, magnetic locating system and acoustic locating system.

159. The method of claim 146, wherein said imaging instrument is a real-time imaging instrument.

160. The method of claim 159, wherein said real-time imaging instrument is selected from the group consisting of ultrasound, fluoroscope and interventional magnetic resonance imaging.

161. The method of claim 146, wherein said imaging instrument is a non-real-time imaging instrument.

162. The method of claim 161, wherein said non-real-time imaging instrument is selected from the group consisting of computer aided tomography (CT), magnetic resonance imaging (MRI), positron emission tomography (PET) and three dimensional ultrasound.

163. The method of claim 146, wherein said imaging instrument provides a primary image of said portion of the body.

164. The method of claim 146, wherein said imaging instrument provides a secondary image of said portion of the body.

165. The method of claim 146, wherein said imaging instrument is designed to provide an image which corresponds to a vitality map of a tissue.

166. The method of claim 146, wherein said imaging instrument is adapted for simultaneously generating at least two images each of a different plane.

167. The method of claim 146, wherein establishing said location of said imaging instrument is effected by attaching a location implement onto said imaging instrument and establishing the location of said imaging instrument via a locating implement.

168. The method of claim 167, wherein said location implement and said locating implement form a locating system selected from the group consisting of electromagnetic locating system, magnetic locating system, acoustic locating system, and stereopair optical system.

169. The method of claim 146, wherein establishing said location of said imaging instrument is effected by image processing of features of the body and by location information regarding said features.

170. The method of claim 169, wherein said features are imageable markers made in contact with the body.

171. The method of claim 169, wherein said features are imageable markers on said at least one catheter.

172. The method of claim 146, wherein establishing said location of said imaging instrument is effected by image processing of features of the body and by magnification information regarding said features.

173. The method of claim 146, wherein establishing said location of said imaging instrument is effected by a positioning implement inherent to said imaging instrument.

174. The method of claim 146, wherein said portion of the body is a cavity within the body.

175. The method of claim 146, wherein said portion of the body is selected from the group consisting of heart, lung, kidney, liver, bladder, brain, colon and a blood vessel.

176. The method of claim 146, wherein said catheter is a probing catheter including at least one sensor.

177. The method of claim 176, wherein said at least one sensor is selected from the group consisting of a sensor for sensing bio-physiology signals, a sensor for sensing electrophysiology signals, a sensor for sensing at least one bio-chemical constituent, a sensor for sensing a bio-mechanical effect, a sensor for sensing a physiopathological character of a tissue and an imaging sensor.

178. The method of claim 146, wherein said catheter is selected from the group consisting of a steerable catheter, a cardiac catheter, an electrophysiology catheter, an ablating catheter and a catheter exerting energy to a tissue.

179. The method of claim 178, wherein said energy is selected from the group consisting of electromagnetic energy, non-coherent light energy, laser energy, microwave energy, mechanical energy, sound energy, ultrasound energy, heating energy and cooling energy.

180. The method of claim 146, wherein said catheter includes an injection device.

181. The method of claim 180, wherein said injection device includes an injection mechanism for injecting a substance or an object into said portion of the body, said substance or object is selected from the group consisting of a glue, micro-coils, micro-spheres, a contrast agent, a growth factor and cells.

182. The method of claim 146, wherein said catheter includes an item selected from the group consisting of a stent delivery device, an expandable balloon, a lead, a mechanism of lead placement, an electrode, a mechanism for electrode placement and a guiding wire.

183. The method of claim 146 wherein said catheter is selected from the group consisting of a guiding catheter, an endoscope, a needle, a surgical tool and a drill for drilling in a tissue of the body.

184. The method of claim 146, wherein said catheter is selected from the group consisting of a catheter for treating fistulae, a catheter for treating arteriovenous malformation (AVM), a catheter for treating aneurism, a catheter for treating stenosis, a a catheter for treating sclerosis, a catheter for treating ischemia, a catheter for treating cardiac arrhytmia, a catheter for treating tremor, a catheter for treating Parkinson's disease, a catheter for treating a tumor (either benign or malignant), a catheter for treating renal calculus and a catheter for treating stomach ulcer.

185. The method of claim 146, wherein said at least one point-of-interest is a reference point which is useful in context of a medical procedure and a point, a size and shape of which is indicative of treatment range applied.

186. The method of claim 146, wherein a plurality of said at least one point-of-interest are arranged in a line.

187. The method of claim 186, wherein said line is selected from the group consisting of a closed line, a boundary line of an internal organ or a portion thereof, a line taken at a given direction along a body tissue and a boundary line between portions of a tissue having different biophysiologic characteristic.

188. The method of claim 187, wherein said biophysiologic characteristic is selected from the group consisting of tissue vitality level, tissue blood perfusion level, tissue temperature level, tissue movement characteristic, tissue density level, tissue texture, tissue chemistry, tissue optical transparency level, local pressure level in said body portion and tissue impedance level.

189. The method of claim 146, wherein said at least one point-of-interest is selected from the group consisting of a portion of a blood vessel, a junction between at least two blood vessels and a displacement relative to another point-of-interest.

190. The method of claim 146, wherein the medical procedure is for treating a medical condition selected from the group consisting of fistulae, arteriovenous malformation (AVM), aneurysm, stenosis, sclerosis, ischemia, cardiac arrhythmia, tremor, Parkinson's disease, malignant tumor and a benign tumor.

191. A method of navigating a catheter's tip to at least one point-of-interest in a body during an intra-body medical procedure, the method comprising the steps of:

(a) establishing a location of the body in such a manner as to establish the location of the body even when the body moves;

(b) establishing a location of an imaging instrument being for imaging at least a portion of the body;

(c) defining at least one projection plane being in relation to a projection plane of said imaging instrument;

(d) inserting a catheter into said portion of the body and establishing a location of said catheter;

(e) projecting at least a portion of said catheter on said at least one projection plane;

(f) acquiring at least one point-of-interest of said portion of the body;

(g) projecting said at least one point-of-interest on said at least one projection plane, such that, in course of said procedure, said locations of said body, said catheter and said imaging instrument are known, thereby said at least one point-of-interest and said at least a portion of said catheter are projectable on said at least one projection plane even in cases whereby a relative location of said body and said imaging instrument are changed; and (h) navigating the catheter's tip to at least one of said points-of-interest.

192. The method of claim 191, further comprising the step of displaying a virtual image of said at least one point-of-interest in context of at least one image representing said at least one projection plane.

193. The method of claim 192, further comprising the step of displaying a virtual image of said at least a portion said catheter in context of said at least one image representing said at least one projection plane.

194. The method of claim 191, further comprising the step of displaying a virtual image of said at least a portion said catheter in context of at least one image representing said at least one projection plane.

195. The method of claim 194, wherein displaying said at least a portion of said catheter in context of said at least one image is effected by averaging its location over at least one cardiac cycle.

196. The method of claim 194, wherein displaying said at least a portion of said catheter in context of said at least one image is effected throughout a duration of a cardiac cycle.

197. The method of claim 194, wherein displaying said at least a portion of said catheter in context of said at least one image is effected by averaging its location over at least one cardiac cycle and also throughout said cardiac cycle.

198. The method of claim 194, wherein displaying said at least a portion of said catheter in context of said at least one image is effected by averaging its location over at least one respiratory cycle.

199. The method of claim 194, wherein displaying said at least a portion of said catheter in context of said at least one image is effected by averaging its location throughout a respiratory cycle.

200. The method of claim 194, wherein displaying said at least a portion of said catheter in context of said at least one image is effected by averaging its location over at least one respiratory cycle and also throughout said respiratory cycle.

201. The method of claim 194, wherein said virtual image of said at least a portion of said catheter is selected from the group consisting of a virtual image of a at least a portion of said catheter projected on said at least one projection plane, a virtual image of a direction of a portion of said catheter projected on said at least one projection plane, a virtual image of a curvature of at least a portion of said catheter projected on said at least one projection plane and a virtual image of an effect exerted on a tissue by said catheter projected on said at least one projection plane.

202. The method of claim 191, wherein establishing said location of the body is effected by attaching a location implement onto said body and establishing the location of the body via a locating implement.

203. The method of claim 202, wherein said location implement and said locating implement form a locating system selected from the group consisting of electromagnetic locating system, magnetic locating system, acoustic locating system, and stereopair optical system.

204. The method of claim 191, wherein establishing said location of the body is effected by image processing of features in an image provided by said imaging instrument.

205. The method of claim 204, wherein said features are imageable markers made in contact with the body.

206. The method of claim 205, wherein said markers are distinguishable from one another.

207. The method of claim 191, wherein establishing said location of the body is synchronized with a physiological activity of the body.

208. The method of claim 191, wherein said catheter includes a plurality of electrodes for simultaneously collecting local electric information from inner walls of a heart cavity.

209. The method of claim 191, wherein said catheter includes a mechanism for measuring a leverage of a steering mechanism of the catheter.

210. The method of claim 191, wherein said catheter includes a location implement locationable via a locating implement.

211. The method of claim 210, wherein said location implement and said locating implement form a locating system selected from the group consisting of electromagnetic locating system, magnetic locating system and acoustic locating system.

212. The method of claim 191, wherein said imaging instrument is a real-time imaging instrument.

213. The method of claim 212, wherein said real-time imaging instrument is selected from the group consisting of ultrasound, fluoroscope and interventional magnetic resonance imaging.

214. The method of claim 191, wherein said imaging instrument is a non-real-time imaging instrument.

215. The method of claim 214, wherein said non-real-time imaging instrument is selected from the group consisting of computer aided tomography (CT), magnetic resonance imaging (MRI), positron emission tomography (PET) and three dimensional ultrasound.

216. The method of claim 191, wherein said imaging instrument provides a primary image of said portion of the body.

217. The method of claim 191, wherein said imaging instrument provides a secondary image of said portion of the body.

218. The method of claim 191, wherein said imaging instrument is designed to provide an image which corresponds to a vitality map of a tissue.

219. The method of claim 191, wherein said imaging instrument is adapted for simultaneously generating at least two images each of a different plane.

220. The method of claim 191, wherein establishing said location of said imaging instrument is effected by attaching a location implement onto said imaging instrument and establishing the location of said imaging instrument via a locating implement.

221. The method of claim 220, wherein said location implement and said locating implement form a locating system selected from the group consisting of electromagnetic locating system, magnetic locating system, acoustic locating system, and stereopair optical system.

222. The method of claim 191, wherein establishing said location of said imaging instrument is effected by image processing of features of the body and by location information regarding said features.

223. The method of claim 222, wherein said features are imageable markers made in contact with the body.

224. The method of claim 222, wherein said features are imageable markers on said at least one catheter.

225. The method of claim 191, wherein establishing said location of said imaging instrument is effected by image processing of features of the body and by magnification information regarding said features.

226. The method of claim 191, wherein establishing said location of said imaging instrument is effected by a positioning implement inherent to said imaging instrument.

227. The method of claim 191, wherein said portion of the body is a cavity within the body.

228. The method of claim 191, wherein said portion of the body is selected from the group consisting of heart, lung, kidney, liver, bladder, brain, colon and a blood vessel.

229. The method of claim 191, wherein said catheter is a probing catheter including at least one sensor.

230. The method of claim 229, wherein said at least one sensor is selected from the group consisting of a sensor for sensing bio-physiology signals, a sensor for sensing electrophysiology signals, a sensor for sensing at least one biochemical constituent, a sensor for sensing a bio-mechanical effect, a sensor for sensing a physiopathological character of a tissue and an imaging sensor.

231. The method of claim 191, wherein said catheter is selected from the group consisting of a steerable catheter, a cardiac catheter, an electrophysiology catheter, an ablating catheter and a catheter exerting energy to a tissue.

232. The method of claim 231, wherein said energy is selected from the group consisting of electromagnetic energy, non-coherent light energy, laser energy, microwave energy, mechanical energy, sound energy, ultrasound energy, heating energy and cooling energy.

233. The method of claim 191, wherein said catheter includes an injection device.

234. The method of claim 233, wherein said injection device includes an injection mechanism for injecting a substance or an object into said portion of the body, said substance or object is selected from the group consisting of a glue, micro-coils, micro-spheres, a contrast agent, a growth factor and cells.

235. The method of claim 191, wherein said catheter includes an item selected from the group consisting of a stent delivery device, an expandable balloon, a lead, a mechanism of lead placement, an electrode, a mechanism for electrode placement and a guiding wire.

236. The method of claim 191, wherein said catheter is selected from the group consisting of a guiding catheter, an endoscope, a needle, a surgical tool and a drill for drilling in a tissue of the body.

237. The method of claim 191, wherein said catheter is selected from the group consisting of a catheter for treating fistulae, a catheter for treating arteriovenous malformation (AVM), a catheter for treating aneurism, a catheter for treating stenosis, a a catheter for treating sclerosis, a catheter for treating ischemia, a catheter for treating cardiac arrhytmia, a catheter for treating tremor, a catheter for treating Parkinson's disease, a catheter for treating a tumor (either benign or malignant), a catheter for treating renal calculus and a catheter for treating stomach ulcer.

238. The method of claim 191, wherein said at least one point-of-interest is a reference point which is useful in context of a medical procedure and a point, a size and shape of which is indicative of treatment range applied.

239. The method of claim 191, wherein a plurality of said at least one point-of-interest are arranged in a line.

240. The method of claim 239, wherein said line is selected from the group consisting of a closed line, a boundary line of an internal organ or a portion thereof, a line taken at a given direction along a body tissue and a boundary line between portions of a tissue having different bio-physiologic characteristic.

241. The method of claim 239, wherein said bio-physiologic characteristic is selected from the group consisting of tissue vitality level, tissue blood perfusion level, tissue temperature level, tissue movement characteristic, tissue density level, tissue texture, tissue chemistry, tissue optical transparency level, local pressure level in said body portion and tissue impedance level.

242. The method of claim 191, wherein said at least one point-of-interest is selected from the group consisting of a portion of a blood vessel, a junction between at least two blood vessels and a displacement relative to another point-of-interest.

243. The method of claim 191, wherein the medical procedure is for treating a medical condition selected from the group consisting of fistulae, arteriovenous malformation (AVM), aneurysm, stenosis, sclerosis, ischemia, cardiac arrhythmia, tremor, Parkinson's disease, malignant tumor and a benign tumor.

244. A method of determining an angle between a surface of a body cavity and a catheter, the method comprising the steps of:

(a) establishing a location of the body;

(b) defining a plurality of projection planes of the body;

(c) inserting said catheter into the body cavity and establishing a location of said catheter;

(d) projecting at least a portion of said catheter on each of said plurality of projection planes; and (e) projecting at least one line along said surface on said plurality of projection planes;

such that, in course of guiding said catheter, said location of said body, said catheter and said line are known, thereby an angle between said catheter and said line is definable.

245. The method of claim 244, wherein said plurality of projection planes include at least two mutually perpendicular planes.

246. The method of claim 244, further comprising the step of displaying a virtual image of said catheter on at least one of said plurality of projection plane.

247. The method of claim 246, further comprising the step of displaying a virtual image of said line on at least one of said plurality of projection plane, thereby displaying an angle between said catheter and said line.

248. The method of claim 244, further comprising the step of displaying a virtual image of said line on at least one of said plurality of projection plane.

249. A system for recording and displaying at least one point-of-interest of a body during an intra-body medical procedure, the system comprising:

(a) a mechanism for establishing a location of the body in such a manner as to establish the location of the body even when the body moves;

(b) a mechanism for establishing a location of an imaging instrument for imaging at least a portion of the body, said mechanism for establishing said location of said imaging instrument being configured to establish said location of said imaging instrument by image processing of features of the body together with magnification information regarding said features;

(c) a mechanism for defining at least one projection plane being in relation to a projection plane of said imaging instrument;

(d) a mechanism for establishing a location of a catheter insertable into said portion of the body;

(e) a mechanism for recording a location of at least one point-of-interest via said location of said catheter by advancing said catheter to said at least one point-of-interest in said portion of the body; and (f) a mechanism for projecting said at least one point-of-interest on said at least one projection plane;

such that, in course of said procedure, said locations of said body and said imaging instrument are known, thereby said at least one point-of-interest is projectable on said at least one projection plane even in cases whereby a relative location of said body and said imaging instrument are changed.

250. The system of claim 249, further comprising a mechanism for displaying a virtual image of said at least one point-of-interest in context of at least one image representing said at least one projection plane.

251. The system of claim 249, wherein said imaging instrument is a three dimensional imaging instrument producing an image by which every picture element represents a coordinate in a three dimensional space, the system further comprising:

(g) a mechanism for selecting at least one picture element; and (h) a mechanism for calculating a location in said three dimensional space of said picture element.

252. The system of claim 249, wherein establishing said location of the body is effected by attaching a location implement onto said body and establishing the location of the body via a locating implement.

253. The system of claim 252, wherein said location implement and said locating implement form a locating system selected from the group consisting of electromagnetic locating system, magnetic locating system, acoustic locating system, and stereopair optical system.

254. The system of claim 249, wherein said mechanism for establishing said location of the body is configured to establish said location by image processing of features in an image provided by said imaging instrument.

255. The system of claim 254, wherein said features are imageable markers made in contact with the body.

256. The system of claim 255, wherein said markers are distinguishable from one another.

257. The system of claim 249, wherein establishing said location of the body is synchronized with a physiological activity of the body.

258. The system of claim 249, wherein said catheter includes a plurality of electrodes for simultaneously collecting local electric information from inner walls of a heart cavity.

259. The system of claim 249, wherein said catheter includes a mechanism for measuring a leverage of a steering mechanism of the catheter.

260. The system of claim 249, wherein said catheter includes a location implement locationable via a locating implement.

261. The system of claim 260, wherein said location implement and said locating implement form a locating system selected from the group consisting of electromagnetic locating system, magnetic locating system and acoustic locating system.

262. The system of claim 249, wherein said imaging instrument is a real-time imaging instrument.

263. The system of claim 262, wherein said real-time imaging instrument is selected from the group consisting of ultrasound, fluoroscope and interventional magnetic resonance imaging.

264. The system of claim 249, wherein said imaging instrument is a non-real-time imaging instrument.

265. The system of claim 264, wherein said non-real-time imaging instrument is selected from the group consisting of computer aided tomography (CT), magnetic resonance imaging (MRI), positron emission tomography (PET) and three dimensional ultrasound.

266. The system of claim 249, wherein said imaging instrument provides a primary image of said portion of the body.

267. The system of claim 249, wherein said imaging instrument provides a secondary image of said portion of the body.

268. The system of claim 249, wherein said imaging instrument is designed to provide an image which corresponds to a vitality map of a tissue.

269. The system of claim 249, wherein said imaging instrument is adapted for simultaneously generating at least two images each of a different plane.

270. The system of claim 249, wherein establishing said location of said imaging instrument is effected by attaching a location implement onto said imaging instrument and establishing the location of said imaging instrument via a locating implement.

271. The system of claim 270, wherein said location implement and said locating implement form a locating system selected from the group consisting of electromagnetic locating system, magnetic locating system, acoustic locating system, and stereopair optical system.

272. The system of claim 249, wherein said portion of the body is a cavity within the body.

273. The system of claim 249, wherein said portion of the body is selected from the group consisting of heart, lung, kidney, liver, bladder, brain, colon and a blood vessel.

274. The system of claim 249, wherein said catheter is a probing catheter including at least one sensor.

275. The system of claim 274, wherein said at least one sensor is selected from the group consisting of a sensor for sensing bio-physiology signals, a sensor for sensing electro-physiology signals, a sensor for sensing at least one bio-chemical constituent, a sensor for sensing a bio-mechanical effect, a sensor for sensing a physiopathological character of a tissue and an imaging sensor.

276. The system of claim 249, wherein said catheter is selected from the group consisting of a steerable catheter, a cardiac catheter, an electrophysiology catheter, an ablating catheter and a catheter exerting energy to a tissue.

277. The system of claim 276, wherein said energy is selected from the group consisting of electromagnetic energy, non-coherent light energy, laser energy, microwave energy, mechanical energy, sound energy, ultrasound energy, heating energy and cooling energy.

278. The system of claim 249, wherein said catheter includes an injection device.

279. The system of claim 278, wherein said injection device includes an injection mechanism for injecting a substance or an object into said portion of the body, said substance or object is selected from the group consisting of a glue, micro-coils, micro-spheres, a contrast agent, a growth factor and cells.

280. The system of claim 249, wherein said catheter includes an item selected from the group consisting of a stent delivery device, an expandable balloon, a lead, a mechanism of lead placement, an electrode, a mechanism for electrode placement and a guiding wire.

281. The system of claim 249, wherein said catheter is selected from the group consisting of a guiding catheter, an endoscope, a needle, a surgical tool and a drill for drilling in a tissue of the body.

282. The system of claim 249, wherein said catheter is selected from the group consisting of a catheter for treating fistulae, a catheter for treating arteriovenous malformation (AVM), a catheter for treating aneurism, a catheter for treating stenosis, a a catheter for treating sclerosis, a catheter for treating ischemia, a catheter for treating cardiac arrhytmia, a catheter for treating tremor, a catheter for treating Parkinson's disease, a catheter for treating a tumor (either benign or malignant), a catheter for treating renal calculus and a catheter for treating stomach ulcer.

283. The system of claim 249, wherein said at least one point-of-interest is a reference point which is useful in context of a medical procedure and a point, a size and shape of which is indicative of treatment range applied.

284. The system of claim 249, wherein a plurality of said at least one point-of-interest are arranged in a line.

285. The system of claim 284, wherein said line is selected from the group consisting of a closed line, a boundary line of an internal organ or a portion thereof, a line taken at a given direction along a body tissue and a boundary line between portions of a tissue having different bio-physiologic characteristic.

286. The system of claim 285, wherein said bio-physiologic characteristic is selected from the group consisting of tissue vitality level, tissue blood perfusion level, tissue temperature level, tissue movement characteristic, tissue density level, tissue texture, tissue chemistry, tissue optical transparency level, local pressure level in said body portion and tissue impedance level.

287. The system of claim 249, wherein said at least one point-of-interest is selected from the group consisting of a portion of a blood vessel, a junction between at least two blood vessels and a displacement relative to another point-of-interest.

288. The system of claim 249, wherein the medical procedure is for treating a medical condition selected from the group consisting of fistulae, arteriovenous malformation (AVM), aneurysm, stenosis, sclerosis, ischemia, cardiac arrhythmia, tremor, Parkinson's disease, malignant tumor and a benign tumor.

289. A system for navigating a catheter's tip to at least one point-of-interest in a body during an intra-body medical procedure, the system comprising:
(a) a mechanism for establishing a location of the body in such a manner as to establish the location of the body even when the body moves;
(b) a mechanism for establishing a location of an imaging instrument being for imaging at least a portion of the body;
(c) a mechanism for defining at least one projection plane being in relation to a projection plane of said imaging instrument;
(d) a mechanism for establishing a location of a catheter being insertable into said portion of the body;
(e) a mechanism for projecting at least a portion of said catheter on said at least one projection plane;
(f) a mechanism for displaying a virtual image of said at least a portion of said catheter in the context of at least one image representing said at least one projection plane;
(g) a mechanism for acquiring at least one point-of-interest of said portion of the body;
(h) a mechanism for projecting said at least one point-of-interest on said at least one projection plane, such that, in course of said procedure, said locations of said body, said catheter and said imaging instrument are known, thereby said at least one point-of-interest and said at least a portion of said catheter are projectable on said at least one projection plane even in cases whereby a relative location of said body and said imaging instrument are changed; and
(i) a mechanism for navigating the catheter's tip to at least one of said points-of-interest,
wherein displaying said at least a portion of said catheter in context of said at least one image is effected throughout a duration of a cardiac cycle.

290. The system of claim 289, further comprising a mechanism for displaying a virtual image of said at least one point-of-interest in context of at least one image representing said at least one projection plane.

291. The system of claim 290, further comprising the a mechanism for displaying a virtual image of said at least a portion said catheter in context of said at least one image representing said at least one projection plane.

292. The system of claim 289, wherein said mechanism for displaying is configured to display said at least a portion of said catheter in context of said at least one image by averaging its location over at least one cardiac cycle.

293. The system of claim 289, wherein said mechanism for displaying is configured to display said at least a portion of said catheter in context of said at least one image by averaging its location over at least one cardiac cycle and also throughout said cardiac cycle.

294. The system of claim 289, wherein said mechanism for displaying is configured to display said at least a portion of said catheter in context of said at least one image by averaging its location over at least one respiratory cycle.

295. The system of claim 289, wherein said mechanism for displaying is configured to display said at least a portion of said catheter in context of said at least one image by averaging its location throughout a respiratory cycle.

296. The system of claim 289, wherein said mechanism for displaying is configured to display said at least a portion of said catheter in context of said at least one image by averaging its location over at least one respiratory cycle and also throughout said respiratory cycle.

297. The system of claim 289, wherein establishing said location of the body is effected by attaching a location implement onto said body and establishing the location of the body via a locating implement.

298. The system of claim 297, wherein said location implement and said locating implement form a locating system selected from the group consisting of electromagnetic locating system, magnetic locating system, acoustic locating system, and stereopair optical system.

299. The system of claim 289, wherein said mechanism for establishing said location of the body is configured to establish said location of the body by imaging processing of features in an image provided by said imaging instruments.

300. The system of claim 299, wherein said features are imageable markers made in contact with the body.

301. The system of claim 300, wherein said markers are distinguishable from one another.

302. The system of claim 289, wherein establishing said location of the body is synchronized with a physiological activity of the body.

303. The system of claim 289, wherein said catheter includes a plurality of electrodes for simultaneously collecting local electric information from inner walls of a heart cavity.

304. The system of claim 289, wherein said catheter includes a mechanism for measuring a leverage of a steering mechanism of the catheter.

305. The system of claim 289, wherein said catheter includes a location implement locationable via a locating implement.

306. The system of claim 305, wherein said location implement and said locating implement form a locating system selected from the group consisting of electromagnetic locating system, magnetic locating system and acoustic locating system.

307. The system of claim 289, wherein said imaging instrument is a real-time imaging instrument.

308. The system of claim 307, wherein said real-time imaging instrument is selected from the group consisting of ultrasound, fluoroscope and interventional magnetic resonance imaging.

309. The system of claim 289, wherein said imaging instrument is a non-real-time imaging instrument.

310. The system of claim 309, wherein said non-real-time imaging instrument is selected from the group consisting of computer aided tomography (CT), magnetic resonance imaging (MRI), positron emission tomography (PET) and three dimensional ultrasound.

311. The system of claim 289, wherein said imaging instrument provides a primary image of said portion of the body.

312. The system of claim 289, wherein said imaging instrument provides a secondary image of said portion of the body.

313. The system of claim 289, wherein said imaging instrument is designed to provide an image which corresponds to a vitality map of a tissue.

314. The system of claim 289, wherein said imaging instrument is adapted for simultaneously generating at least two images each of a different plane.

315. The system of claim 289, wherein establishing said location of said imaging instrument is effected by attaching a location implement onto said imaging instrument and establishing the location of said imaging instrument via a locating implement.

316. The system of claim 315, wherein said location implement and said locating implement form a locating system selected from the group consisting of electromagnetic locating system, magnetic locating system, acoustic locating system, and stereopair optical system.

317. The system of claim 289, wherein establishing said location of said imaging instrument is effected-by image processing of features of the body and by location information regarding said features.

318. The system of claim 317, wherein said features are imageable markers made in contact with the body.

319. The system of claim 317, wherein said features are imageable markers on said at least one catheter.

320. The system of claim 289, wherein establishing said location of said imaging instrument is effected by image processing of features of the body and by magnification information regarding said features.

321. The system of claim 289, wherein establishing said location of said imaging instrument is effected by a positioning implement inherent to said imaging instrument.

322. The system of claim 289, wherein said portion of the body is a cavity within the body.

323. The system of claim 289, wherein said portion of the body is selected from the group consisting of heart, lung, kidney, liver, bladder, brain, colon and a blood vessel.

324. The system of claim 289, wherein said virtual image of said at least a portion of said catheter is selected from the group consisting of a virtual image of a at least a portion of said catheter projected on said at least one projection plane, a virtual image of a direction of a portion of said catheter projected on said at least one projection plane, a virtual image of a curvature of at least a portion of said catheter projected on said at least one projection plane and a virtual image of an effect exerted on a tissue by said catheter projected on said at least one projection plane.

325. The system of claim 289, wherein said catheter is a probing catheter including at least one sensor.

326. The system of claim 325, wherein said at least one sensor is selected from the group consisting of a sensor for sensing bio-physiology signals, a sensor for sensing electrophysiology signals, a sensor for sensing at least one biochemical constituent, a sensor for sensing a bio-mechanical effect, a sensor for sensing a physiopathological character of a tissue and an imaging sensor.

327. The system of claim 289, wherein said catheter is selected from the group consisting of a steerable catheter, a cardiac catheter, an electrophysiology catheter, an ablating catheter and a catheter exerting energy to a tissue.

328. The system of claim 327, wherein said energy is selected from the group consisting of electromagnetic energy, non-coherent light energy, laser energy, microwave energy, mechanical energy, sound energy, ultrasound energy, heating energy and cooling energy.

329. The system of claim 289, wherein said catheter includes an injection device.

330. The system of claim 329, wherein said injection device includes an injection mechanism for injecting a substance or an object into said portion of the body, said substance or object is selected from the group consisting of a glue, micro-coils, micro-spheres, a contrast agent, a growth factor and cells.

331. The system of claim 289, wherein said catheter includes an item selected from the group consisting of a stent delivery device, an expandable balloon, a lead, a mechanism of lead placement, an electrode, a mechanism for electrode placement and a guiding wire.

332. The system of claim 289, wherein said catheter is selected from the group consisting of a guiding catheter, an endoscope, a needle, a surgical tool and a drill for drilling in a tissue of the body.

333. The system of claim 289, wherein said catheter is selected from the group consisting of a catheter for treating fistulae, a catheter for treating arteriovenous malformation (AVM), a catheter for treating aneurism, a catheter for treating stenosis, a a catheter for treating sclerosis, a catheter for treating ischemia, a catheter for treating cardiac arrhytmia, a catheter for treating tremor, a catheter for treating Parkinson's disease, a catheter for treating a tumor (either benign or malignant), a catheter for treating renal calculus and a catheter for treating stomach ulcer.

334. The system of claim 289, wherein said at least one point-of-interest is a reference point which is useful in context of a medical procedure and a point, a size and shape of which is indicative of treatment range applied.

335. The system of claim 289, wherein a plurality of said at least one point-of-interest are arranged in a line.

336. The system of claim 335, wherein said line is selected from the group consisting of a closed line, a boundary line of an internal organ or a portion thereof, a line taken at a given direction along a body tissue and a boundary line between portions of a tissue having different bio-physiologic characteristic.

337. The system of claim 336, wherein said bio-physiologic characteristic is selected from the group consisting of tissue vitality level, tissue blood perfusion level, tissue temperature level, tissue movement characteristic, tissue density level, tissue texture, tissue chemistry, tissue optical transparency level, local pressure level in said body portion and tissue impedance level.

338. The system of claim 289, wherein said at least one point-of-interest is selected from the group consisting of a portion of a blood vessel, a junction between at least two blood vessels and a displacement relative to another point-of-interest.

339. The system of claim 289, wherein the medical procedure is for treating a medical condition selected from the group consisting of fistulae, arteriovenous malformation (AVM), aneurysm, stenosis, sclerosis, ischemia, cardiac arrhythmia, tremor, Parkinson's disease, malignant tumor and a benign tumor.

340. A system for determining an angle between a surface of a body cavity and a catheter, the system comprising:
  (a) a mechanism for establishing a location of the body;
  (b) a mechanism for defining a plurality of projection planes of the body;
  (c) a mechanism for establishing a location of a catheter insertable into the body cavity;
  (d) a mechanism for projecting at least a portion of said catheter on each of said plurality of projection planes; and
  (e) a mechanism for projecting at least one line along said surface on said plurality of projection planes;
such that, in course of guiding said catheter, said location of said body, said catheter and said line are known, thereby an angle between said catheter and said line is definable.

341. The system of claim 340, wherein said plurality of projection planes include at least two mutually perpendicular planes.

342. The system of claim 340, further comprising a mechanism for displaying a virtual image of said catheter on at least one of said plurality of projection plane.

343. The system of claim 340, further comprising a mechanism for displaying a virtual image of said line on at least one of said plurality of projection plane.

344. The system of claim 342, further comprising a mechanism for displaying a virtual image of said line on at least one of said plurality of projection plane, thereby displaying an angle between said catheter and said line.

345. A system for navigating a catheter's tip to at least one point-of-interest in a body during an intra-body medical procedure, the system comprising:
- (a) a mechanism for establishing a location of the body in such a manner as to establish the location of the body even when the body moves;
- (b) a mechanism for establishing a location of an imaging instrument being for imaging at least a portion of the body;
- (c) a mechanism for defining at least one projection plane being in relation to a projection plane of said imaging instrument;
- (d) a mechanism for establishing a location of a catheter being insertable into said portion of the body;
- (e) a mechanism for projecting at least a portion of said catheter on said at least one projection plane;
- (f) a mechanism for displaying a virtual image of said at least a portion of said catheter in the context of at least one image representing said at least one projection plane;
- (g) a mechanism for acquiring at least one point-of-interest of said portion of the body;
- (h) a mechanism for projecting said at least one point-of-interest on said at least one projection plane, such that, in course of said procedure, said locations of said body, said catheter and said imaging instrument are known, thereby said at least one point-of-interest and said at least a portion of said catheter are projectable on said at least one projection plane even in cases whereby a relative location of said body and said imaging instrument are changed; and
- (i) a mechanism for navigating the catheter's tip to at least one of said points-of-interest, wherein said mechanism for displaying is configured to display said at least a portion of said catheter in context of said at least one image by averaging its location over at least one cardiac cycle and also throughout said cardiac cycle.

346. A system for navigating a catheter's tip to at least one point-of-interest in a body during an intra-body medical procedure, the system comprising:
- (a) a mechanism for establishing a location of the body in such a manner as to establish the location of the body even when the body moves;
- (b) a mechanism for establishing a location of an imaging instrument being for imaging at least a portion of the body;
- (c) a mechanism for defining at least one projection plane being in relation to a projection plane of said imaging instrument;
- (d) a mechanism for establishing a location of a catheter being insertable into said portion of the body;
- (e) a mechanism for projecting at least a portion of said catheter on said at least one projection plane;
- (f) a mechanism for displaying a virtual image of said at least a portion of said catheter in the context of at least one image representing said at least one projection plane;
- (g) a mechanism for acquiring at least one point-of-interest of said portion of the body;
- (h) a mechanism for projecting said at least one point-of-interest on said at least one projection plane, such that, in course of said procedure, said locations of said body, said catheter and said imaging instrument are known, thereby said at least one point-of-interest and said at least a portion of said catheter are projectable on said at least one projection plane even in cases whereby a relative location of said body and said imaging instrument are changed; and
- (i) a mechanism for navigating the catheter's tip to at least one of said points-of-interest, wherein said mechanism for displaying is configured to display said at least a portion of said catheter in context of said at least one image by averaging its location throughout a respiratory cycle.

347. A system for navigating a catheter's tip to at least one point-of-interest in a body during an intra-body medical procedure, the system comprising:
- (a) a mechanism for establishing a location of the body in such a manner as to establish the location of the body even when the body moves;
- (b) a mechanism for establishing a location of an imaging instrument being for imaging at least a portion of the body;
- (c) a mechanism for defining at least one projection plane being in relation to a projection plane of said imaging instrument;
- (d) a mechanism for establishing a location of a catheter being insertable into said portion of the body;
- (e) a mechanism for projecting at least a portion of said catheter on said at least one projection plane;
- (f) a mechanism for displaying a virtual image of said at least a portion of said catheter in the context of at least one image representing said at least one projection plane;
- (g) a mechanism for acquiring at least one point-of-interest of said portion of the body;
- (h) a mechanism for projecting said at least one point-of-interest on said at least one projection plane, such that, in course of said procedure, said locations of said body, said catheter and said imaging instrument are known, thereby said at least one point-of-interest and said at least a portion of said catheter are projectable on said at least one projection plane even in cases whereby a relative location of said body and said imaging instrument are changed; and
- (i) a mechanism for navigating the catheter's tip to at least one of said points-of-interest, wherein said mechanism for displaying is configured to display said at least a portion of said catheter in context of said at least one image by averaging its location over at least one respiratory cycle and also throughout said respiratory cycle.

* * * * *